US012402952B2

(12) United States Patent
Mucha et al.

(10) Patent No.: US 12,402,952 B2
(45) Date of Patent: Sep. 2, 2025

(54) REGISTRATION METHOD AND NAVIGATION SYSTEM

(71) Applicant: Intersect ENT International GmbH, Hennigsdorf (DE)

(72) Inventors: Dirk Mucha, Glienicke/Nordbahn (DE); Kai Desinger, Berlin (DE); Nicholas Norman, Charlotte, NC (US); Robert Hedermann, Berlin (DE)

(73) Assignee: Fiagon GMBH, Henningsdorf (DE)

( * ) Notice: Subject to any disclaimer, the term of this patent is extended or adjusted under 35 U.S.C. 154(b) by 408 days.

(21) Appl. No.: 17/715,595

(22) Filed: Apr. 7, 2022

(65) Prior Publication Data
US 2022/0273375 A1 Sep. 1, 2022

Related U.S. Application Data

(63) Continuation of application No. PCT/EP2020/078634, filed on Oct. 12, 2020.

(30) Foreign Application Priority Data

Oct. 10, 2019 (DE) ..................... 10 2019 127 387.0

(51) Int. Cl.
*A61B 34/20* (2016.01)
*A61B 10/02* (2006.01)
(Continued)

(52) U.S. Cl.
CPC ............ *A61B 34/20* (2016.02); *A61B 10/025* (2013.01); *A61B 10/0283* (2013.01);
(Continued)

(58) Field of Classification Search
CPC ... A61B 34/20; A61B 10/025; A61B 10/0283; A61B 2010/0258; A61B 2034/2051;
(Continued)

(56) References Cited

U.S. PATENT DOCUMENTS 6,314,310 B1 * 11/2001 Ben-Haim ............. A61B 34/20
606/130
2016/0249984 A1 * 9/2016 Janssen .................. A61B 34/25
600/427

FOREIGN PATENT DOCUMENTS

EP 3456274 A1 * 3/2019 ......... A61B 17/1703

* cited by examiner

*Primary Examiner* — David P Porta
*Assistant Examiner* — Casey Bryant
(74) *Attorney, Agent, or Firm* — Nancy C. Wilker

(57) ABSTRACT

The invention relates to a method for automatically registering an object, the method comprising the steps of
providing a preoperatively obtained model of the object,
providing at least one marker carrier having a plurality of fluoroscopically detectable makers and at least one marker localization element fixed on it, wherein the at least one marker localization element being configured to provide a sensor signal representing position and orientation of the marker localization element in an electromagnetic field, and relative distance and orientation between at least one marker localization element and at least one marker of the plurality of markers are known,
arranging the at least one marker carrier on an outer surface of the object,
generating at least one fluoroscopic image of at least one marker carrier arranged on the outer surface together with at least one segment of the object in such a way that at least two markers of at least one marker carrier are visible in the generated fluoroscopic image together with at least one segment of the object,
determining position and orientation at least of one marker localization element of the arranged marker carrier in an electromagnetic field, and
relating image points of the generated fluoroscopic image to model points of said preoperatively obtained model
(Continued)

using the determined position and orientation of at least one marker localization element and the known relative distance and orientation between at least one maker localization element and at least one marker of the plurality of markers and/or a known spatial relation between a further marker of the plurality of markers and the at least one marker that has a known relative distance and orientation to at least one maker localization element.

27 Claims, 7 Drawing Sheets

(51) Int. Cl.
*A61B 90/00* (2016.01)
*G06T 7/246* (2017.01)
*G06T 7/33* (2017.01)

(52) U.S. Cl.
CPC .............. *G06T 7/251* (2017.01); *G06T 7/344* (2017.01); *A61B 2010/0258* (2013.01); *A61B 2034/2051* (2016.02); *A61B 2034/2072* (2016.02); *A61B 2090/376* (2016.02); *A61B 2090/3966* (2016.02); *A61B 2090/397* (2016.02); *G06T 2207/10064* (2013.01); *G06T 2207/30012* (2013.01); *G06T 2207/30204* (2013.01)

(58) Field of Classification Search
CPC ...... A61B 2034/2072; A61B 2090/376; A61B 2090/3966; A61B 2090/397; A61B 90/39; G06T 7/251; G06T 7/344; G06T 2207/10064; G06T 2207/30012; G06T 2207/30204; G06T 2207/10081; G06T 2207/10088; G06T 2207/10121; G06T 7/33
See application file for complete search history.

REGISTRATION METHOD AND NAVIGATION SYSTEM

CROSS-REFERENCE TO RELATED APPLICATIONS

This application is a continuation of International Patent Application No. PCT/EP2020/078634, filed Oct. 12, 2020, which claims priority to German Patent Application No. 10 2019 127 387.0, filed Oct. 10, 2019, each of which is incorporated herein by reference in its entirety.

TECHNICAL FIELD

The invention relates to a registration method for automatically registering an object. The invention also relates to a navigation system that is configured for performing such a registration method.

BACKGROUND OF THE INVENTION

For assisting a surgeon in using a medical instrument in a surgical procedure it is known to track the position of the medical instrument inside a patient's body and to display the instrument's position in, e.g., sectional images of a model of a patient on a monitor.

To this end, navigation systems are used typically comprising a data processing unit, a monitor, a number of localization elements and a position detection system. The position detection system can be, e.g., an optical, an ultrasound-based or an electromagnetic position detection system. A position detection system, in general, is configured for determining position and orientation of localization elements.

By way of example, electromagnetic position detection systems are known having a field generator for generating an alternating electromagnetic field. A medical instrument to be used with an electromagnetic position detection system is equipped with a localization element that typically comprises one or more coils.

When exposed to the alternating electromagnetic field, in the coils of a localization element a voltage is induced that depends on the position and orientation of a respective coil in the alternating electromagnetic field. By analysing a tapped voltage signal representing the induced voltage, position and orientation of the localization element can be determined. Typically, position and orientation of a localization element of a medical instrument are determined relative to the position and orientation of a reference localization element that can likewise comprise coils and that stays fixed relative to a patient.

To be able to display the instrument's position in sectional images of a patient's model on a monitor of a navigation system, initially, the model has to be registered. Typically, the model of a patient is a topographic image that is generated from two-, three- or four-dimensional images of a patient obtained preoperatively by tomography, e.g., via computed tomography (CT), magnetic resonance imaging (MRI) or C-arm fluoroscopic imaging. Initially, the model is defined in terms of coordinates in the coordinate system of the respective two, three- or even four-dimensional image.

Registration refers to obtaining the spatial correlation between position and orientation of a patient in real space (sometimes also called patient space) and the model defined in terms of coordinates in the coordinate system of the respective two-, three- or four-dimensional image used for generating the model. In particular, for obtaining the spatial correlation between patient and model, a transformation function is established that defines how to relate a coordinate, e.g., in patient space, to a respective coordinate of a model point of the model of a patient and vice versa.

For establishing a transformation function within the scope of a registration method various approaches are known, e.g., surface-based registration and point-based registration.

In point-based registration, markers arranged on a patient or anatomical landmarks used as fiducial points, respectively, are employed for establishing a reference coordinate system at the patient and at the patient model generated from a two-, three- or four-dimensional image of the patient.

Point-based registration can be performed, e.g., by touching these markers or landmarks with a pointer instrument or sensing instrument that is tracked with a position detection system. By touching markers or landmarks with a tracked instrument, points on the real surface of a patient are identified and the corresponding position values of a localization element that are determined with a position detection system are related to respective model points of the model representing the same marker or landmark positions. From the positions of the markers or landmarks, a reference coordinate system is established at the model and at the patient and from the reference coordinate systems the needed transformation function is determined.

If the model is registered to the patient, the position of a medical instrument can be displayed in sectional images of the model for assisting a surgeon in navigating the medical instrument. For displaying the position of a medical instrument in sectional images of the model, determined position and orientation of a medical instrument's localization element are transformed into a respective coordinate of a model point of the model of a patient.

SUMMARY OF THE INVENTION

It is an object to provide an improved registration method for automatically registering an object and to provide an improved navigation system that is configured for performing the automatic registration method.

Regarding the registration method, the object is achieved by a registration method for automatically registering an object. The registration method comprises the steps of
  providing a preoperatively obtained model of the object,
  providing at least one marker carrier having a plurality of fluoroscopically detectable makers and at least one marker localization element fixed on it, wherein the at least one marker localization element being configured to provide a sensor signal representing position and orientation of the marker localization element in an alternating electromagnetic field, and wherein relative distance and orientation between at least one marker localization element and at least one marker of the plurality of markers are known,
  arranging at least one marker carrier on an outer surface of the object,
  generating at least one fluoroscopic image of at least one marker carrier arranged on the outer surface together with at least one segment of the object in such a way that at least two markers of at least one marker carrier are visible in the generated fluoroscopic image together with at least one segment of the object,
  determining position and orientation at least of one marker localization element of the arranged marker carrier in an electromagnetic field, and relating image points of the generated fluoroscopic image to model points of the preoperatively obtained model.

Relating image points of the generated fluoroscopic image to model points of the preoperatively obtained model can be performed using the determined position and orientation of at least one marker localization element and the known relative distance and orientation between at least one maker localization element and at least one marker of the plurality of markers.

Additionally or alternatively to using the known relative distance and orientation between at least one maker localization element and at least one marker of the plurality of markers, relating image points of the generated fluoroscopic image to model points of said preoperatively obtained model can be performed using a known spatial relation between a further marker of the plurality of markers and the at least one marker that has a known relative distance and orientation to at least one maker localization element.

Of these steps, the step of "generating at least one fluoroscopic image of at least one marker carrier" can be performed before or after or, as it is preferred, simultaneously to the step of "determining position and orientation at least of one marker localization element".

With the registration method according to the invention an object can automatically be registered without the need of contacting markers or landmarks with a pointer instrument or sensing instrument.

In particular, with the registration method according to the invention it is possible to register an object comprising several elements that can move relative to each other and to maintain the registration accuracy over the duration of a navigated procedure even if the elements of the object move relative to each other during the navigated procedure.

To maintain the registration accuracy over the duration of a navigated procedure also when elements of the object move relative to each other is achieved by the registration method according to the invention in that the object is registered segmentwise, i.e., segment by segment.

Segmentwise registration refers to dividing the object into segments and to establishing an individual transformation function for each of the object's segments. Preferably, each segment is associated with a respective marker carrier that is arranged on the respective segment. It is possible that a plurality of marker carriers is arranged on respective segments of an object. It is also possible that a marker carrier is displaced segment by segment for registering an object.

A size of a segment can be defined according to various criteria. In case the object comprises a plurality of elements, each of the object's segments can comprise a different one of the object's elements, i.e., one element per segment. It is also possible that one segment comprises two or more elements of the object. In case one segment comprise two or more elements, the size of a segment can be chosen the way that a relative movement between two or more elements comprised by the segment is negligible for the registration accuracy. It is also possible that the way of segmentation is already suggested by the shape of the object itself, e.g., if the object is a patient's spine one segment can include one or more vertebras.

In the registration method according to the invention, initially, a marker carrier and a preoperatively obtained model of the object are provided.

The preoperatively obtained model can be generated from image data recorded, e.g., by tomography. The model can be a 2D or 3D or 4D model of the object. Preferably, however, the model is a 3D model generated from 2D fluoroscopic images that are registered to a 3D model. Initially, the model is defined via coordinates of the image data from which the model is generated, e.g., via coordinates of a tomographic image of a patient.

The at least one marker carrier used within the registration method according to the invention is characterized in that it has a plurality of fluoroscopically detectable makers and at least one marker localization element fixed on it wherein relative distance and orientation between the at least one marker localization element and at least one marker of the plurality of markers are known.

The known relative distance and orientation between the at least one marker localization element and at least one marker of the plurality of markers refers to the relative distance and orientation between the at least one marker localization element and at least one marker being fixed, i.e., constant with respect to each other, and being available prior to registering the object.

In particular, the known spatial relation is an inherent geometric property of the marker carrier and thus available prior to registration. The know spatial relationship is provided as an input for the navigation system and the registration method in form of fixed geometry data. The fixed geometry data, preferably, are provided by way of a constant vector or matrix that represents the spatial relation between the at least one marker localization element and at least one marker of the plurality of markers. For example, the geometry data can form a vector defining the spatial relation between the at least one marker localization element and at least one marker of the plurality of markers in the coordinate system of the marker localization element.

In case the spatial relations between the marker localization element and several markers and/or the spatial relation between several markers are known, the known spatial relations can be provided as an input for the navigation system and the registration method in form of geometry data set comprising the respective geometry data.

The fluoroscopically detectable makers can be, e.g., gold plates that are distributed over the surface of the marker carrier. In general, the makers are fluoroscopically detectable because they are made of a material that is either more or less radiopaque than the marker carrier itself. However, preferably, the fluoroscopically detectable makers are configured in that they can be used as fiducial points in a generated fluoroscopic image. The fluoroscopically detectable makers, e.g., can have a zero-dimensional or also a one-dimensional geometry.

The marker localization element affixed to the marker carrier can be arranged at the position of a fluoroscopically detectable maker, i.e., congruently. The marker localization element can also be arranged at a position that is different from the positions at which fluoroscopically detectable makers are arranged. However, it is required that the at least one marker localization element has a known relative distance and orientation to at least one of the plurality of fluoroscopically detectable markers. This known spatial relation between the at least one marker localization element and at least one of the plurality of fluoroscopically detectable markers allows to determine the position at least of the marker with known spatial relation in a position detection system's coordinate system and, vice versa, the position of the marker localization element in the coordinate system of a generated fluoroscopic image.

The marker localization element is configured for capturing an electromagnetic field, e.g., an alternating electromagnetic field, and for providing a sensor signal representing position and orientation of the marker localization element in the electromagnetic field. The provided sensor signal can be transmitted via a cable or wirelessly to a position detection system that is configured to determine position and orientation of the marker localization element by analysing the received sensor signal.

Preferably, the marker localization element comprises one or more sensor coils. The marker localization element, preferably, is configured to capture six degrees of freedom (DOF). Such a six DOF marker localization element can be implemented in that it comprises at least two sensor coils that are arranged at an angle, e.g., orthogonally, to each other. If the marker localization element comprises one or more coils, a voltage signal can be tapped representing position and orientation of the marker localization element in the alternating electromagnetic field and transmitted to a position detection system.

A marker carrier with localization element can also be used as a reference localization element for navigating a medical instrument that is likewise equipped with a localization element relative to the marker carrier in an electromagnetic field generated by a field generator of a position detection system. A marker carrier with localization element can also be used as reference localization element for tracking the position of one or more further marker localization elements of respective further marker carriers relative to the position of a marker carrier's localization element that is used as reference localization element.

For the registration method according to the invention, the marker carrier is arranged on an outer surface of the object. It is preferred that the marker carrier stays on the outer surface of the object during a navigated procedure such that registration can be performed several times without moving the marker carrier itself. It is also possible that for each registration the marker carrier is arranged on the object's outer surface and removed afterwards. A transformation function can than repeatedly determined during a navigated procedure and can be updated with each newly performed registration. By repeatedly updating an established transformation function registration maintained accurate even if elements of the object move relative to each other during a navigated procedure.

An object to be registered can comprise a plurality of elements that can move relative to each other. For example, the object having several elements can be a patient's spine with the elements being the spine's vertebras. If the object is a spine, the marker carrier can be arranged directly on the exposed spine or on the skin of a patient, e.g., at a distance above the patient's spine. Arranging the marker carrier on an outer surface of the object can also refer to a situation in which the marker carrier is arranged on a patient's skin at a distance to an actual structure of interest, e.g., a patient's spine. Preferably, the marker carrier is arranged on the outer surface of an object such that in a projection of the object that is visible in a generated fluoroscopic image, at least two of the fluoroscopically detectable markers of the marker carrier are visible together with a structure of interest, e.g., three to four vertebras of a patient's spine.

Of the at least one marker carrier arranged on the outer surface of the object at least one fluoroscopic image is generated such that in the fluoroscopic image at least two markers of the marker carrier are visible together with at least one segment of the object. The fluoroscopic image comprises image points that for generating the fluoroscopic image are reconstructed from fluoroscopic image data recorded, e.g., with an X-ray device having an X-ray source and an X-ray detector.

A segment, preferably, refers to a limited area of the outer surface of the object. Taking the example of the object being a spine, the segment refers, e.g., to a spine's vertebra. Preferably, three to four vertebras with at least one of them having a marker carrier arranged on it are visible in a generated fluoroscopic image. It is also possible that a segment of a spine comprises more than one vertebra, e.g., two, three or four vertebras. The subdivision of the object to be registered into segments can, e.g., be chosen such that each segment comprises a different one of the object's elements or such that a relative movement of two or more elements comprised by a respective segment is negligible with regard to the registration accuracy. Advantageously, with the automatic registration method according to the invention it is possible to detect a relative movement between two or more segments of the object.

The area of a segment can be larger than that part of the outer surface that is covered by a marker carrier.

Since the marker carrier comprises at least one marker localization element that is configured to provide a sensor signal representing position and orientation of the marker localization element, position and orientation of the at least of one marker localization element can be determined, e.g., by a position detection system that is configured to analyse the provided sensor signal. In general, a position detection system is configured to determine position and orientation of the at least of one marker localization element in the position detection system's coordinate system.

Position and orientation of the marker carrier being arranged on the outer surface of an object can be calculated by means of the determined position and orientation of at least one marker localization element. With the marker carrier being arranged on the outer surface of the object, that position and orientation of the marker localization element can be determined that correspond to a point on the outer surface of the object in real space, e.g. patient space. This allows establishing a reference coordinate system at the object, e.g., by transforming the position detection system's coordinate system such that its origin is that point on the object's surface that has a known spatial relation to the marker carrier's marker localization element.

Since the at least one marker localization element has a known relative distance and orientation to at least one marker of the plurality of markers of the marker carrier, it is possible to calculate the coordinate of this marker with known spatial relation in the position detection system's coordinate system and in real space, i.e., relative to a point on the outer surface of the object. The fluoroscopically detectable markers can be used as artificial landmarks that in a conventional registration method would have been touched with a tracked pointer instrument or sensing instrument. By means of that determined position of the marker localization element that corresponds to a point on the real surface of the object, a reference coordinate system can be established at the object. For establishing a reference coordinate system at the object, additionally, the known spatial relation of at least one fluoroscopically detectable marker that has a known spatial relation to the marker localization element can be used.

To find a transformation function, the reference coordinate system needs also to be established at the preoperatively obtained model.

In the registration method according to the invention establishing a reference coordinate system at the model is achieved via generating a fluoroscopic image of the marker carrier together with at least one segment of the object. In a generated fluoroscopic image at least two fluoroscopically detectable markers are visible that—due to the known spatial relation between at least one marker of the marker carrier and the at least one marker localization element—can be expressed in terms of coordinates in real space of the object. By relating image points of the fluoroscopic image, e.g., representing anatomical landmarks, to respective model points of the preoperatively obtained model it is possible to establish a reference coordinate system at the preoperatively obtained model and to find the transformation function for transforming a model point into a coordinate in real space of the object and vice versa. After registration was carried out, the position of a tracked medical instrument that is navigated relative to the marker carrier can be displayed in sectional images of the preoperatively obtained model that is visualized on a monitor.

The registration method according to the invention can be repeated several times during the duration of a navigated procedure such that the registration can be updated and maintained accurate.

With the registration method according to the invention it is possible to register a plurality of individual segments of an object and, in particular, segments of this object on which marker carriers are arranged, several times during a navigated procedure. Advantageously, with each performed registration a transformation function is established according to the actual shape of the object at the moment of registration. The frequency with which registration of the object is performed can be adapted according, e.g., to a relative movement between the object's elements exceeding a predefined threshold value. When navigating a medical instrument from segment to segment of the object, the respective transformation function of the respective segment can be used for accurately displaying the position of the medical instrument in sectional images of the preoperatively obtained model of the object.

In the following, preferred variants of the registration method according to the invention are described.

Preferably, the model points are points of a model surface of the preoperatively obtained model wherein the model surface corresponds to the outer surface of the object. The model surface can be a topographic image of the object. The model points and thus the preoperatively obtained model can be generated from a two-, three- or four-dimensional image obtained via tomography.

In a variant of the automatic registration method according to the invention the marker carrier that is arranged on the outer surface of the object is flexible, i.e., it can adapt its shape to the topography of the outer surface. The flexible marker carrier can, e.g., be a belt or have the shape of a belt. Preferably, fluoroscopically detectable markers are fixed at stationary positions on the flexible marker carrier. The flexible marker carrier can have such a stiffness that it cannot be stretched so that relative positions of markers fixed on the flexible marker carrier are maintained.

In this variant of the registration method in which a flexible marker carrier is used,
- a flexible marker carrier is arranged on the object's outer surface,
- the plurality of markers is fixed in such a way on said marker carrier that respective groups of three markers each form a pattern that can be distinguished from patterns formed by other marker groups in the generated fluoroscopic image, and
- at least two segments of the object are identifiable in the at least one generated fluoroscopic image in that each of the segments is assigned to a different pattern formed by said markers.

The flexible marker carrier is characterized in that the fluoroscopically detectable markers are arranged such that respective groups of at least three markers each form a pattern that is unique on the flexible marker carrier. For example, if a group comprises three markers that form a triangle, the triangle can be distinguished from other patterns formed by respective other groups of the markers.

Each of the marker patterns can be assigned to or can be used to define or to identify a different segment of several segments of the object. Due to the plurality of several distinguishable patterns, the flexible marker carrier can be interpreted as several individual marker carriers stitched together each of the individual marker carriers having an individual marker pattern.

When generating a fluoroscopic of the flexible marker carrier such that at least two segments of the object are identifiable by means of respectively associated marker patterns, it is possible to reconstruct the topography of the object at least within these two segments. Reconstruction of the topography of the object can be achieved because of the marker patterns associated to each of the segments, respectively, being visible in the generated fluoroscopic image together with the segments. Since the marker carrier is flexible, each of the patterns can be visible in a deformed manner corresponding to the topography of the object's outer surface. From the deformation of a pattern and the spatial relation between respective patterns being visible in a generated fluoroscopic image together with the segments, the topography of the outer surface can be computationally reconstructed.

Landmarks of the generated topography and, in particular, image points of the fluoroscopic image representing these landmarks can be assigned to corresponding model points of the preoperatively obtained model in order to find a transformation function within the scope of the automatic registration method according to the invention.

In another variant of the registration method according to the invention several marker carriers, i.e., at least two marker carriers are arranged simultaneously on the outer surface of the object. The marker carriers used can be configured identically or can be configured differently. Preferably, the marker carriers used are rigid, i.e., non-flexible.

In this variant in which several marker carriers are arranged simultaneously on the outer surface of the object
- at least two marker carriers are simultaneously arranged on the object's outer surface,
- the at least one fluoroscopic image is generated of at least two segments of the object in such a way that for each segment at least two markers of an arranged marker carrier are visible in the generated fluoroscopic image together with the respective segment, and
- a spatial relation between the segments of which the fluoroscopic image was generated is determined using positions of those markers that are visible in the generated fluoroscopic image.

For example, the several marker carriers can be arranged along a spine, e.g., directly along an exposed spine or on a patient's skin at a distance above the spine. Since each of the marker carriers comprises at least one marker localization element, position and orientation of each of the marker carriers can be tracked independently with a position detection system. It is advantageous if the marker carriers are classified or labelled. For example, for tracking each marker carrier independently the marker carriers being arranged the outer surface of the object can be simply labelled with numbers 1, 2, 3, etc. The marker carriers can be arranged on the object's outer surface in different patterns, e.g., as a cluster or along a line. It is preferred, if the markers are arranged on that part of the outer surface of the object that is expected to change its shape, i.e., on a part of the object comprising several elements that can move relative to each other. To register an object segmentwise, by means of the plurality of marker carriers, that part of the object that comprises several elements that can move relative to each other can be divided into segments each comprising one or more elements such that each segment of the object can be registered individually.

Preferably, if the object is a spine, in the generated fluoroscopic image three to four vertebras, e.g., segments, are visible. At or above of each of the vertebras a respective marker carrier can be arranged such that each of the vertebras can be registered and tracked individually.

Advantageously, since the marker carriers are arranged simultaneously on the outer surface of the object, for generating the fluoroscopic image fluoroscopic image data have to be recorded once, only, such that X-ray exposure of the object can be reduced.

It is possible to use one of the marker carrier's localization elements as reference localization element for tracking the position of other marker carriers and/or for tracking the position of a medical instrument equipped with a localization element relative to this reference localization element.

Since the fluoroscopic image is generated in such a way that at least two segments and for each of the segments at least two markers of a respectively arranged marker carrier are visible, it is possible to determine a spatial relation between the segments visible based on the positions of the visible markers that are respectively assigned to one of the segments. Determining a spatial relation between the segments using the positions of the markers visible in the fluoroscopic image can be achieved because the at least two markers that are visible for each segment have a known spatial relation to each other. The known spatial relation of markers of a respective segment can be used for determining a spatial relation between these markers and markers of neighbouring segments that are also visible in the generated fluoroscopic image. From the determined spatial relation of the segments, the topography of the object can be reconstructed and/or a relative movement of the segments can be detected.

In yet another variant of the registration method according to the invention, the marker carrier is displaced segment by segment. If, for example, the object is a spine, the marker carrier can be displaced vertebra by vertebra and at each position a fluoroscopic image is generated. Each of the generated fluoroscopic images can be used to register a respective segment individually. It is also possible to stitch all fluoroscopic images once they have been generated and to use the stitched fluoroscopic image for registering the object.

In the variant of the automatic registration according to the invention in which the marker carrier is displaced step by step in successive steps the marker carrier is arranged on the object's outer surface,
in each of the successive steps a fluoroscopic image of the arranged marker carrier together with at least one segment is generated in such a way that at least two markers of the marker carrier are visible in the fluoroscopic image together with a respective segment of the object, and
a spatial relation between the segments of which the fluoroscopic images were generated is determined using positions of those markers that are visible in the respective fluoroscopic images.

In this variant it is also possible that one marker carrier, e.g., the one that is arranged on the first segment of the object, stays on the object's outer surface while a further marker carrier is displaced from segment to segment for registering the object. The marker carrier that remains on the outer surface can be used as a reference localization element for tracking the relative position of the further marker carrier and/or for tracking the relative position of a medical instrument hat is equipped with an instrument localization element and navigated relative to the object.

Also in the variant in which the marker carrier is displaced step by step, a spatial relation between the segments of which the fluoroscopic images were generated can be determined using positions of those markers that are visible in the respective fluoroscopic images. From the determined spatial relation between the segments the topography of the object can be reconstructed and/or a relative movement of the segments can be detected.

Preferably, in the automatic registration methods described herein for each generated fluoroscopic image of one or more segments, image points of a respective one of these fluoroscopic images are segmentally, i.e., segmentwise, related to model points of said preoperatively obtained model. Accordingly, for each segment an individual transformation function can be established. For displaying the position of a medical instrument in sectional images of the preoperatively obtained model of the object, the transformation function applied can be chosen according to the segment in which the medical instrument is currently located.

It is an advantage of segmentally registering the object that from the registration of individual segments a registration error can be determined. In particular, a registration error can be determined from image points of at least two segments that are related to respective model points and a known spatial relation between the at least two segments. This is possible since for each segment an individual transformation function is established. The outcome of a coordinate transformation using each of the established transformation functions can be compared to determine a registration error. The transformation functions can be updated or corrected in order to remedy the determined registration error to improve registration accuracy for each individual segment.

The automatic registration methods described herein can comprise the step of
visualizing the preoperatively obtained model on an image display unit, e.g., a monitor of a navigation system, in such a way that depending on the relating of image points to model points the visualized model is aligned such that the viewing direction on said model on the image display unit corresponds to the recording direction from which fluoroscopic image data used for generating the fluoroscopic image of at least one segment were recorded.

If the visualized model is aligned to the projection visible in the fluoroscopic image, it can be easier for a user to compare the generated fluoroscopic image to the preoperatively obtained model that is visualized on a monitor during a navigated procedure. Alignment of the viewing direction on the model to the perspective of the generated fluoroscopic image can be achieved since the spatial relation of coordinates of image points and model points, e.g., defined in an established reference coordinate system, can be analysed and the viewing direction on the model adapted accordingly. In dependence on the relating of image points to model points, the model can be visualized on an image display unit such that the viewing direction on the model corresponds to the viewing direction on the generated fluoroscopic image.

The automatic registration methods described herein can also comprise the step of
  detecting a relative movement of an element of the object by determining a deviation of at least one model point of the preoperatively obtained model from a corresponding image point of the generated fluoroscopic image.

If an element of the object moves relative to other elements or relative to a reference localization element after initial registration, a transformation function established for a segment of the object can become inaccurate such that image points are related to model points that do not represent the same feature of the object as the image point. If automatic registration according to the invention is carried out again, a new transformation function is established such that an image point is related to a corresponding model point that is different from the model point that corresponded to the same image point before relative movement of an element of the object. A deviation, e.g., a deviation vector in a reference coordinate system, of the new corresponding model point to the prior corresponding model point can be calculated and from that a relative movement of an element of the object can be detected. For example, a relative movement of a spine's vertebra can be detected intraoperatively during surgery.

An automatic registration method according to the invention comprising the step of "detecting a relative movement of an element of the object by determining a deviation of a model point from a corresponding image point" as described before can also comprise the additional step of
  segmentally adapting the preoperatively obtained model of the object using the determined deviation.

Hence, the preoperatively obtained model generated from two-, three- or four-dimensional images of a patient obtained by tomography can be adapted based on the determined deviation. If the model is updated based on a determined deviation, a user can use a model that represents an actual shape of an object that has changed its shape since generating the preoperatively obtained model prior to a navigated procedure or since the las adaptation of the model during a navigated procedure. Advantageously, due to the segmentally performed registration for each segment an individual deviation can be determined such that the model can be adapted segmentwise. Segmentally adapting the preoperatively obtained model, preferably, is performed intraoperatively by a navigation system that is configured to execute an accordingly implemented algorithm.

In particular, an automatic registration method in which a relative movement of an element of an object is detected by means of determining a deviation of a model point from a corresponding image point that optionally can also comprise that a preoperatively obtained model is segmentally adapted according to the determined deviation as described before can also comprise the steps of
  providing an instrument having an instrument localization element for determining position and orientation in an electromagnetic field,
  determining position and orientation of the instrument localization element in an electromagnetic field relative to the position and orientation of at least one marker localization element,
  visualizing the adapted model of the object on an image display unit together with at least a part of said instrument,
  wherein position and orientation of said instrument in the visualization of said model are adapted using the determined deviation of at least one model point from a corresponding image point of the generated fluoroscopic image.

A marker localization element of the at least one marker carrier that is arranged on the outer surface of the object can be used as a reference localization element for an instrument, e.g., a medical instrument, that is likewise equipped with an instrument localization element. If the preoperatively obtained model is registered to the object, a position icon or a digital representation at least of a part of the instrument can be displayed in the preoperatively obtained model of the object such that a user can orient oneself on the displayed model when navigating the instrument relative to the object.

Since the preoperatively obtained model can be adapted according to a determined deviation of a model point from a corresponding image point, it is preferred, to likewise adapt the position of the instrument in an adapted model in order to provide a representation that is as close as possible to the actual navigation situation. For transforming the position of an instrument into the coordinate of a corresponding model point of an adapted model, the determined deviation, e.g., a deviation vector, can be used. If model and position of an instrument in the model are adapted according to a determined deviation, a user can navigate an instrument relative to the object in a precise manner and navigation errors caused by an inaccurate representation of the instrument's position in the visualized model can be avoided.

In an automatic registration method in which the position and orientation of an instrument in the visualization of the model are adapted using a determined deviation of at least one model point from a corresponding image point of the generated fluoroscopic image, preferably, adapting position and orientation of the instrument in the visualization of the adapted model is performed segmentally for each segment of the object that is visible in the generated fluoroscopic image. Segmentally adapting position and orientation of the instrument in the visualization of the adapted model is possible since within the scope of the automatic registration method according to the invention for each segment an individual registration function is established that can be employed for the adaptation of position and orientation of the instrument in a respective one of the segments.

Automatic registration methods described herein can comprise the steps of
  arranging at least one reference localization element in a fixed spatial relation to the object, the at least one reference localization element being configured to provide a reference sensor signal representing position and orientation of the reference localization element in an electromagnetic field, and
  determining position and orientation of at least one marker localization element in an electromagnetic field relative to position and orientation of at least one reference marker localization.

The reference localization element, sometimes also called patient localizer, can be an additional element of a navigation system. Preferably, such a reference localization element is arranged fixed relative to the object. The reference localization element can be arranged next to the object or can be rigidly attached to the object itself. Position and orientation of the reference localization element can be determined by a position detection system that is configured for analysing a provided reference sensor signal representing position and orientation of the reference localization element in an electromagnetic field.

Relative to position and orientation of the reference localization element, position and orientation of at least one marker localization element of a marker carrier can be determined by a position detection system having a field generator for generating an electromagnetic field, e.g., an alternating electromagnetic field.

In particular, if at least one reference localization element is arranged next to or arranged attached to the object, when conducting the registration method according to the invention, the automatic registration method can comprise the steps of determining position and orientation of at least one marker localization element relative to at least one reference localization element at a first instant of time and at a later further instant of time, and detecting a change in position and/or orientation of the marker localization element relative to position and orientation of at least one reference localization element at the later instant of time in relationship to the earlier first instant of time.

The position and orientation of the marker localization element can be tracked relative to the reference localization element. Additionally, also the position and orientation of an instrument equipped with an instrument localization element can be tracked either relative to the reference localization element or relative to the marker localization element or relative to both of them. By detecting a change in position and/or orientation of the marker localization element relative to position and orientation of a reference localization element at the later instant of time in relationship to the earlier first instant of time it is possible to detect a relative movement of the object, in particular, of an element of the object, during a navigated procedure. The information about the object or at least one of the object's elements having moved relative to the reference localization element can be used to trigger a new automatic registration of the object for updating at least one established transformation function. Since a marker carrier is associated to a respective segment of the object, it is possible to detect a relative movement of a specific segment with respect to, e.g., another segment or a reference localization element. Since the relative movement of an individual segment can be detected, it is possible to only update the transformation function related to this specific object while transformation functions established for other segments in which no relative movement was detected can still be applied.

If the automatic registration method according to the invention is conducted for registering a patient's spine, the automatic registration method can be specified in that the object is a patient's spine and the at least one segment of the spine comprises one or more vertebras, the preoperatively obtained model is a model of at least a part of the spine, the at least one marker carrier is arranged on the spine, at least one fluoroscopic image is generated of at least the segment comprising the vertebra that has the marker carrier arranged on it in such a way that at least two of the plurality of fluoroscopically detectable markers of the marker carrier are visible together with at least one vertebra, and for each generated fluoroscopic image of one or more vertebras, image points of a respective one of these fluoroscopic images are segmentally related to model points of the preoperatively obtained spine model.

Preferably, the segment comprises one or two vertebras and the fluoroscopic image is generated in such a way that three to four vertebras are visible. The marker carrier can be arranged directly on one or more vertebras of an exposed spine or can be arranged on the outer skin of a patient and thus at a distance above the respective one or more vertebras.

In an automatic registration method according to the invention in which the object is a spine it is particularly preferred that image points of the fluoroscopic image that represent a vertebra are related to respective model points of the same vertebra in the preoperatively obtained spine model. The vertebras can be used as anatomical landmarks for registering the spine.

In an automatic registration method according to the invention in which the object is a spine, several marker carriers can be arranged simultaneously along the spine for automatically registering the spine. An automatic registration method in which several marker carriers are arranged simultaneously along the spine, e.g., during spine surgery, can comprise that at least one fluoroscopic image is generated at least of the vertebras that have the marker carriers arranged on it, and for each generated fluoroscopic image, image points of the fluoroscopic image that represent a vertebra are related to corresponding model points representing the same vertebra in the preoperatively obtained spine model.

By way of relating an image point representing a point on a vertebra is related to a corresponding model point representing the same point on the vertebra model, each vertebra can be registered individually, i.e., segmentally vertebra by vertebra, such that as a result of the segmentwise registration for each vertebra an individual transformation function can be established. As a result of segmentally registering a spine, a movement of each of the vertebras relative to the other spine vertebras or relative to a reference localization element can be tracked individually. In case a relative movement of a vertebra is detected, the corresponding transformation function can be updated by registering the respective vertebra again.

A relative movement of a spine or a spine's vertebra can be detected, e.g., intraoperatively, by determining a deviation of at least one model point of the preoperatively obtained spine model from a corresponding image point of the generated fluoroscopic image.

Advantageously, the automatic registration methods described herein can be conducted prior to spine surgery for planning a procedure or during spine surgery for registering a patient's spine for assisting a surgeon in performing the procedure.

For example, spinal fusion can be performed comprising preoperatively or intraoperatively registering the spine using at least one marker carrier that is arranged on a vertebra or using at least one marker carrier being arranged on the spine only for intraoperatively registering the spine and being removed afterwards. During spine surgery, the at least one marker carrier can be arranged for registration and removed afterwards several times in order to repeatedly update one or more established transformation functions.

In spinal fusion performed on a spine that is registered by applying the automatic registration method according to the invention, for example, two or more vertebras can be joint by means of a pedicel screw, a plate or a cage. By means of spinal fusion, e.g., spinal stenosis, spondylolisthesis, spondylosis, spinal fractures, vertebral fracture, a spinal tumor scoliosis, the posterior rami syndrome, degenerative disc diseases, spinal disc herniation, discogenic pain or kyphosis can be treated.

If the object is a spine that is automatically registered by conducting the registration method according to the invention using at least one marker carrier that is arranged on a vertebra for intraoperatively registering the spine or using at least one marker carrier that is arranged on the spine only for intraoperatively registering the spine and that is removed afterwards, e.g., in spine surgery, a polyaxial screw can be screwed into a respective vertebra having the at least one marker carrier arranged on it. Typically, in spinal surgery polyaxial screws are used for connecting vertebras to rods, e.g., for treating degenerative cervical spondylosis and curvatures. Preferably, the position of the screw can be tracked with a position detection system, e.g., by arranging a localization element at or in the polyaxial screw.

During surgery, the position of a tracked polyaxial screw can be displayed in the spine model for assisting a surgeon in placing the polyaxial screw.

In particular, prior to or during minimally invasive spine surgery, automatic registration methods described herein can be used to register the spine. For registering a spine as part of minimally invasive spine surgery, at least one marker carrier can be arranged on a vertebra for intraoperatively registering the spine or at least one marker carrier can be arranged on the spine only for intraoperatively registering the spine and can be removed afterwards.

Minimally invasive spine surgery in which a spine is registered by conducting the automatic registration method according to the invention can include anterior cervical discectomy, artificial disc replacement or total disc replacement, epidural lysis of adhesions, laminectomy, laminotomy, oblique lateral lumbar inter body fusion (OLLIF), percutaneous vertebroplasty, endoscopic discectomy. Minimally invasive spine surgery on a registered spine can be performed for the treatment of degenerative disc diseases, disc herniation, fractures, tumors, infections, instability, and deformity.

It is also of advantage to register a spine by conducting the automatic registration method as described herein in case bone marrow biopsy shall be performed on the spine. Preferably, the spine that is subject to bone marrow biopsy is registered with at least one marker carrier being arranged on a vertebra for intraoperatively registering the spine or with at least one marker carrier being arranged on the spine only for intraoperatively registering the spine and removed afterwards. With bone marrow biopsy it is possible to establish a diagnostic on several conditions, including leukaemia, multiple myeloma, lymphoma, anaemia, and pancytopenia.

Into a spine that is registered by conducting an automatic registration method as described herein also a Jamshidi needle can be inserted. A Jamshidi needle is a cannulated needle with a tapered cutting tip with which bone marrow biopsy can be performed. The Jamshidi needle itself can be connected to a position detection system in that it comprises an instrument localization element. With a position detection system, it is possible to track the position of the Jamshidi needle equipped with a localization element relative to the position of at least one of the marker carriers arranged on the patient's body and/or relative to the position of a reference localization element. The position of the Jamshidi needle can be displayed in the preoperatively obtained model of the patient such that a surgeon can follow the position of the Jamshidi needle in the patient's body and in particular the penetration of the Jamshidi needle into the vertebral body in tomographically obtained sectional images of the vertebral body virtually on a monitor.

Another medical instrument that can be used in a surgical procedure performed on a patient that is registered by performing the registration method according to the invention is a hollow needle that is configured for use in fine-needle aspiration biopsy (FNAB). The patient can be automatically registered with at least one marker carrier being arranged on the patient for intraoperatively registering the patient or with at least one marker carrier being arranged on the patient only for intraoperatively registering the patient and removed afterwards and a hollow needle can be inserted into a patient's body for performing fine-needle aspiration biopsy (FNAB). Preferably, the hollow needle is equipped with a localization element that is used for tracking the position of the hollow needle relative to a patient when guiding the hollow needle to a target location that can be a spine or a different body part of a patient.

In an automatic registration method for registering a spine with at least one marker carrier being arranged on a vertebra for intraoperatively registering the spine or the at least one marker carrier being arranged on the spine only for intraoperatively registering the spine and removed afterwards, a cannulated medical instrument, such as a catheter ort a hollow needle, comprising at least one instrument localization element for providing position and orientation information can be inserted into a patient's body. The instrument localization element can be arranged in such a way in, e.g., a lumen of the cannulated medical instrument such that it can be removed, e.g., after the medical instrument being navigated to a target location inside a patient's body. The position of the medical instrument equipped with an instrument localization element can be tracked with a position detection system relative to a patient and, e.g., relative to a marker localization element and/or relative to a reference localization element. After the instrument localization element has been removed from a lumen of the medical instrument the lumen can be used, e.g., for suction or irrigation purposes, e.g., for delivering medication to a patient.

In an automatic registration method for registering a spine as described herein also at least one marker carrier can be arranged on a vertebra for intraoperatively registering the spine or at least one marker carrier can be arranged on the spine only for intraoperatively registering the spine and removed afterwards and a cannulated medical instrument can be inserted into a patient's body for providing a working channel for an additional medical instrument. Preferably, the additional medical instrument comprises at least one instrument localization element for providing position and orientation information. The position of the additional medical instrument being guided through the working channel of the cannulated medical instrument can be displayed in a preoperatively obtained model on a monitor of a navigation system.

A marker carrier that can be used in the automatic registration methods described herein can be implemented in various shapes, e.g., in the shape of a cage, a plate, a stick, a cylinder, a cube, etc., and can be made of various materials or material combinations, preferably, synthetic materials like silicones. In particular, marker carriers that can be used in the automatic registration methods described herein can be realised in the shape of the reference bodies shown in and described with respect to FIGS. 4 to 9 in WO 2014/184382 A1. Preferably, a marker carrier that can be used in the automatic registration methods described herein has a size that allows to arrange a plurality of fluoroscopically detectable markers such that they can be identified as individual markers in a generated fluoroscopic image. Preferably, a marker carrier that is used in an automatic registration method according to the invention is made of a material that is less radiopaque than the fluoroscopically detectable markers fixed on it. A marker carrier that is used in an automatic registration method according to the invention can be made of a material that is substantially transparent for X-rays.

Marker carriers that can be used in the automatic registration methods described herein have in common that they have a plurality of fluoroscopically detectable makers and at least one marker localization element fixed on it. The at least one marker localization element is configured to provide a sensor signal representing position and orientation of the marker localization element in an alternating electromagnetic field. In particular, relative distance and orientation between at least one marker localization element and at least one marker of the plurality of markers of a marker carrier are known.

With respect to the navigation system, the aforementioned object is achieved by a navigation system that is configured for performing a registration method according to one of the automatic registration methods described herein. The navigation system comprises at least one marker carrier, a position detection system, an X-ray device and a registration unit.

The at least one marker carrier has a plurality of fluoroscopically detectable makers and at least one marker localization element fixed on it. The at least one marker localization element is configured to provide a sensor signal representing position and orientation of the marker localization element in an electromagnetic field. The marker localization element and at least one of the plurality of fluoroscopically detectable markers are arranged such that relative distance and orientation between the at least one marker localization element and the at least one marker of the plurality of markers are known.

If the marker carrier is arranged on the outer surface of an object, that position of the marker localization element can be determined with the position detection system that corresponds or can be related to a position on the outer surface of the object in real space. Since at least one of the fluoroscopically detectable markers has a known spatial relation to the marker localization element, the position of the point on the outer surface of the object in real space can be transformed into a coordinate of a model point of the preoperatively obtained model via an established transformation function via the navigation system's registration unit.

The position detection system has a field generator for generating an electromagnetic field, e.g., an alternating electromagnetic field. The position detection system is configured for determining position and orientation at least of the marker localization element in an electromagnetic field.

The X-ray device has an X-ray source and an X-ray detector for recording fluoroscopic image data from which a fluoroscopic image at least of the marker carrier can be generated such that at least two markers of the marker carrier are visible in the generated fluoroscopic image. The X-ray device, for example, can be a C-arm.

The registration unit is configured for relating image points of a generated fluoroscopic image to model points of a preoperatively obtained model. The registration unit, in particular, is connected to the position detection system to access and use a determined position and orientation of at least one marker localization element. The registration unit is also configured for processing image information of a fluoroscopic image that can be, e.g., generated by the registration unit itself or by another suitable processing unit that is configured for reconstructing fluoroscopic image points from fluoroscopic image data recorded with the X-tray device in order to generate the fluoroscopic image.

In particular, the registration unit is configured for using a determined position and orientation of at least one marker localization element and the known relative distance and orientation between at least one maker localization element and at least one marker of the plurality of markers and/or a known spatial relation between a further marker of the plurality of markers and the at least one marker that has a known relative distance and orientation to at least one maker localization element.

The known spatial relation between a marker localization element and at least one of the markers can be expressed, e.g., in terms of a vector pointing from the coordinate of the marker localization element to the coordinate of a marker. For example, the vector can be defined in the coordinate system of the marker localization element. With a position detection system, position and orientation of the marker localization element's coordinate system can be determined relative to a position detection system's coordinate system that, e.g., can be associated with a field generator. The vector representing the known spatial relation can be transformed into different coordinate systems, e.g., and used to establish a transformation function within the scope of the automatic registration method according to the invention.

The registration unit is configured to establish a transformation function for transforming coordinates between a reference coordinate system established at the object and at the preoperatively obtained model by relating image points of a generated fluoroscopic image to model points of a preoperatively obtained model. The registration unit can be part of a data processing unit of the navigation system or a separate component connected, e.g., to a data processing unit and/or a monitor of the navigation system. It is particularly preferred that the registration unit is configured in such a way that if the generated fluoroscopic image shows one or more segments, for each generated fluoroscopic image of one or more segments, image points of a respective one of these fluoroscopic images can be segmentally related to model points of the preoperatively obtained model. The registration unit can be configured to identify and/or define segments of the object according to markers of respective marker carriers that are visible in a generated fluoroscopic image.

An instrument, e.g., a medical instrument, that comprises an instrument localization element can be connected to the navigation system. This allows tracking a position of the instrument relative to an object and, e.g., relative to a reference localization element or relative to a marker localization element that is used as a reference localization element. The position of the tracked instrument can be displayed to a user in a preoperatively obtained model of the object for assisting the user in navigating the instrument.

BRIEF DESCRIPTION OF THE DRAWINGS

In the following, preferred embodiments of the invention are described with reference to the figures. In the figures.

DETAILED DESCRIPTION

Figure 1:
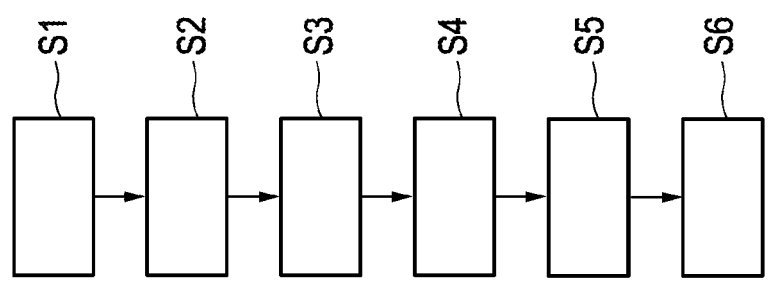
FIG. 1: shows a flow diagram representing a registration method for automatically registering an object.

FIG. 1 shows a flow diagram representing a method for automatically registering an object.

In step S1 of the method, a preoperatively obtained model of the object is provided. The model can be a 2D, 3D, or 4D model that is generated from 2D, 3D, or 4D image data that were recorded by means of tomography. For example, the preoperatively obtained model can be generated from 2D fluoroscopic images that are registered to a 3D model. The model can be generated as a topographic image of the object such that it represents the outer surface of the object or at least a part of the object.

For assisting a user in navigating an instrument relative to the object, the model can be displayed on a monitor of a navigation system. If the instrument is equipped with an instrument localization element, the position of the instrument can be tracked with a position detection system of the navigation system for displaying the instrument's position in the model of the object.

In order to be able to display a position of the instrument in a visualized model, e.g., in terms of an icon or in terms of a digital representation of the instrument, initially, the model needs to be registered to the object.

In the automatic registration method, registration is performed using one or more marker carriers which are initially provided in step S2. At least one of the marker carriers has a plurality of fluoroscopically detectable markers and at least one marker localization element fixed on it. In particular, the one or more marker carriers used in the registration method can be configured the same way as the marker carriers that are described with reference to FIGS. 3 to 7.

The marker localization element can comprise one or more sensor coils, e.g., two sensor coils being arranged orthogonal to each other and being configured for capturing an electromagnetic field. An electromagnetic field, for example, an alternating electromagnetic field, to be captured by the marker localization element can be an electromagnetic field that is generated by a field generator of a navigation system. An electromagnetic field captured by the marker localization element induces a voltage in the sensor coils that depends on position and orientation of the marker localization element in the electromagnetic field. From a tapped sensor signal representing the voltage induced in the sensor coils, position and orientation of the marker localization element can be derived, for example, by a position detection system that is connected to the marker localization element via a cable for receiving the sensor signal. In particular, with a marker localization element comprising two orthogonally arranged sensor coils, it is possible to determine position and orientation in six degrees of freedom.

The fluoroscopically detectable markers of a marker carrier can be, e.g., gold plates. The fluoroscopically detectable markers of the marker carrier can serve as fiducial points in a generated fluoroscopic image.

For at least one marker carrier that has fluoroscopically detectable markers and at least one marker localization element fixed on it, relative distance and orientation between the at least one marker localization element and at least one marker of the plurality of fluoroscopically detectable markers are known.

In particular, the known spatial relation is available a priori in form of fixed geometry data and can provided as an input to the automatic registration method, e.g., by means of a constant vector or matrix representing the fixed spatial relation between the at least one marker localization element and at least one marker of the plurality of fluoroscopically detectable markers.

For example, the geometry data can be provided in form of a vector initially representing the spatial relation between marker localization element and marker in the marker localization element's coordinate system. Within the scope of the registration method, the vector can be transformed into, e.g., a reference coordinate system for registering the object.

For conducting the automatic registration method, in step S3 at least one marker carrier is arranged on the outer surface of the object. In various variants of the registration method, two or more marker carriers are arranged on the outer surface of the object simultaneously. In other variants of the registration method, one or more marker carriers are arranged in successive steps on the object's outer surface.

In step S4, of the at least one marker carrier that is arranged on the outer surface of the object at least one fluoroscopic image is generated together with at least one segment of the object. The fluoroscopic image, in particular, is generated in such a way that at least two markers of an arranged marker carrier are visible in the generated fluoroscopic image together with at least one segment of the object.

Preferably, the area of a segment of the object is defined such that a relative movement of elements comprised by the segment is negligible with respect to the registration accuracy. For example, the object itself can be divided into as many segments as are required to ensure that within the area of each of the segments a potential relative movement between two respective points is negligible. Within the scope of the registration method a relative movement of the segments with respect to each other can be determined. Preferably, on each of the segments a marker carrier is arranged and associated to the respective segment. For generating a fluoroscopic image of the object, a plurality of marker carriers can be arranged on respective segments of the object. In a variant of the automatic registration method, a marker carrier is displaced segment by segment and at each step of arranging the marker carrier a fluoroscopic image is generated of the marker carrier together with the respective segments on which the marker carrier is arranged. A fluoroscopic image is generated from prior recorded fluoroscopic image data.

If a plurality of marker carriers is arranged on the outer surface of the object, preferably, the at least one fluoroscopic image is generated in such a way that at least two markers of each of the arranged marker carriers are visible together with a respective segment. Preferably, in the at least one generated fluoroscopic image several segments and for each segment at least two markers of a respective marker carrier that this arranged on this segment are visible. In case a plurality of markers have a known spatial relation to each other, each of the at least two markers that are visible together with a respective segment can be used to calculate the coordinates of markers that are not visible in the coordinate system of the fluoroscopic image, e.g., for reconstructing a topography of an object. It is beneficial if the marker carriers that are arranged simultaneously on the object are labelled, for example, with numbers 1, 2, 3, etc. Labelling of marker carriers is advantageous for relating visible markers to corresponding segments. Since several segments and for each of the segments at least two markers are visible in the generated fluoroscopic image, it is possible to determine a spatial relation between the segments by means of the positions of those markers that are visible in the generated fluoroscopic image.

If in the automatic registration method, a marker carrier is arranged in successive steps on the object's outer surface, in each of the successive steps a fluoroscopic image can be generated of the marker carrier and at least that segment on which the marker carrier is arranged. As a result, in each successive step an individual fluoroscopic image of the marker carrier and a respective segment is generated. The fluoroscopic images generated in successive steps can be generated such that they have an overlap with their respective neighbouring fluoroscopic images.

Each of the individual fluoroscopic images can be used for segmentally registering the model to respective segments of the object. It is also possible that the fluoroscopic images are stitched to a larger fluoroscopic image which shows all segments of which fluoroscopic images were generated. In a stitched fluoroscopic image, preferably, for each segment on which the marker carrier was arranged in successive steps, at least two fluoroscopically detectable markers are visible together with the respective segment. A stitched fluoroscopic image that shows several segments and for each segment at least two associated markers is similar to a fluoroscopic image that is generated of a plurality of marker carriers arranged simultaneously on the object. If several individual fluoroscopic images are stitched to one fluoroscopic image, the stitched fluoroscopic image can be used for registering the preoperatively obtained model to the object. From the several individual fluoroscopic images, stitched or not stitched, it is possible to determine a spatial relation between the segments by using the positions of the markers that are visible in the respective fluoroscopic image.

For registering the object, it is also possible to use a flexible marker carrier, for example, a belt, having a plurality of fluoroscopically detectable markers and at least one marker localization element fixed on it. The flexible marker carrier can be arranged on the outer surface of the object and can adopt its shape to the topography of the outer surface. Preferably, the fluoroscopically detectable markers are fixed to the belt in such a way on the flexible marker carrier that respective groups of at least three markers each form a pattern that can be distinguished from patterns formed by other groups of markers in a generated fluoroscopic image. Since each group of at least three markers can be distinguished from another group of at least three markers, segments of the object are identifiable in a generated fluoroscopic image by relating a segment to a respective group of markers.

Using groups of at least three markers is advantageous since from the deformation of, e.g., a triangle formed by a group of three markers that are visible in the generated fluoroscopic image, it is possible to determine the orientation of the triangle with respect to the outer surface of the object, and, in particular, to an associated segment of the object. Since several of such groups of at least three markers are fixed on the marker carrier, for several segments the orientation of a respective group of markers to the surface of the respective segment can be determined. This information can be used to reconstruct the topography of the outer surface of the object.

Before generating at least one fluoroscopic image or at the same time of generating at least one fluoroscopic image or after generating at least one fluoroscopic image, in step S5 of the automatic registration method position and orientation of at least one marker localization element of a marker carrier that is arranged on the outer surface of the object is determined. Determining position and orientation of a marker localization element can be performed, for example, with a position detection system of a navigation system.

Since the marker carrier with the marker localization element is arranged on the outer surface of the object, the determined position and orientation of the marker localization element can be related to the position of a point on the outer surface of the object in real space. The determined position and orientation of the marker localization element that can be related to a point on the object's outer surface can be used for establishing a reference coordinate system at the object.

The reference coordinate system can be established at the object using the determined position and orientation of the marker localization element and positions of fluoroscopically detectable markers. This is possible since relative distance and orientation between the at least one marker localization element and at least one marker of the plurality of markers are known.

For registering the object, the reference coordinate system also needs to be established at the preoperatively obtained model in order to find a transformation function for transforming coordinates between the two reference coordinate systems.

For establishing the reference coordinate system at the preoperatively obtained model, in step S6 of the automatic registration method image points of the generated fluoroscopic image are related to model points of the preoperatively obtained model. For relating image points of the fluoroscopic image to respective model ponds of the model, the known spatial relation between the marker localization element and at least one of the fluoroscopically detectable markers can be used. Alternatively or additionally, to using the known spatial relation between the marker localization element and at least one of the fluoroscopically detectable markers, also position and orientation of the marker localization element and a known spatial relation between another marker and the at least one marker that has a known spatial relation to the marker localization element can be used. Furthermore, the position of a point on the outer surface of the object in real space for which a respective coordinate in the position detection system's coordinate system can be determined by detecting position and orientation of the marker localization element can be used, e.g., for relating a point on the real surface of the object to a model point of the preoperatively obtained model.

Advantageously, in the automatic registration method for each generated fluoroscopic image, image points can be segmentally related to model points of the preoperatively obtained model. Segmentally relating image points to model points can comprise relating image points of a segment of the object to model points of the corresponding segment of the preoperatively obtained model of the object. For example, artificial or anatomical landmarks can be identified and an image point representing this landmark can be related to a corresponding model point. Segmentwise registration comprises establishing for each segments an individual transformation function which can be updated independently of transformation functions established for other segments. Segmentwise registration allows to detect a relative movement of a specific segment relative to other segments and/or relative to a reference localization element and to register this specific segment again to update the transformation function associated with this segment to maintain a high registration accuracy.

Since for each of the respective segments of the object an individual transformation function can be established, it is possible to detect a registration error which can be corrected for improving the registration accuracy. A registration error can occur already in the initial registration, for example, caused by fluctuations of the electromagnetic field, or it can occur after initial registration, for example, caused by a relative movement of one or more of the object's elements. Detecting a registration error is possible since the several established transformation functions can be analysed and respective coordinate transformations can be compared, also intraoperatively during a navigated procedure.

Due to the segmentwise registration it is also possible to detect a relative movement of at least one of the object's elements relative to other segments or relative to a reference localization element. If a relative movement of one of the object's elements is detected, one or more transformation functions associated to segments which have moved, e.g., relative to other segments, can be updated by repeating registration of the respective segments. In particular, a relative movement of an element of the object can be detected by determining a deviation of at least one model point of the preoperatively obtained model from a corresponding image point of the fluoroscopic image. A determined deviation can represent a measure for the element's relative movement, for example, in terms of a deviation vector defining direction and relative distance of the element's relative movement.

It is an advantage of the automatic registration method that the object can be registered segmentwise. The automatic registration method is particularly suitable for registering individual segments of an object that comprises a plurality of elements that can move relative to each other. For example, the object can be a patient's spine and a segment can be a vertebra. For registering a spine, for example, several marker carriers can be arranged along the spine to define segments comprising, for example, one or more vertebras that can be registered individually. A relative movement between a plurality of segments can be tracked segmentwise and transformation functions can be updated according to a detected relative movement between segments.

Figure 2:
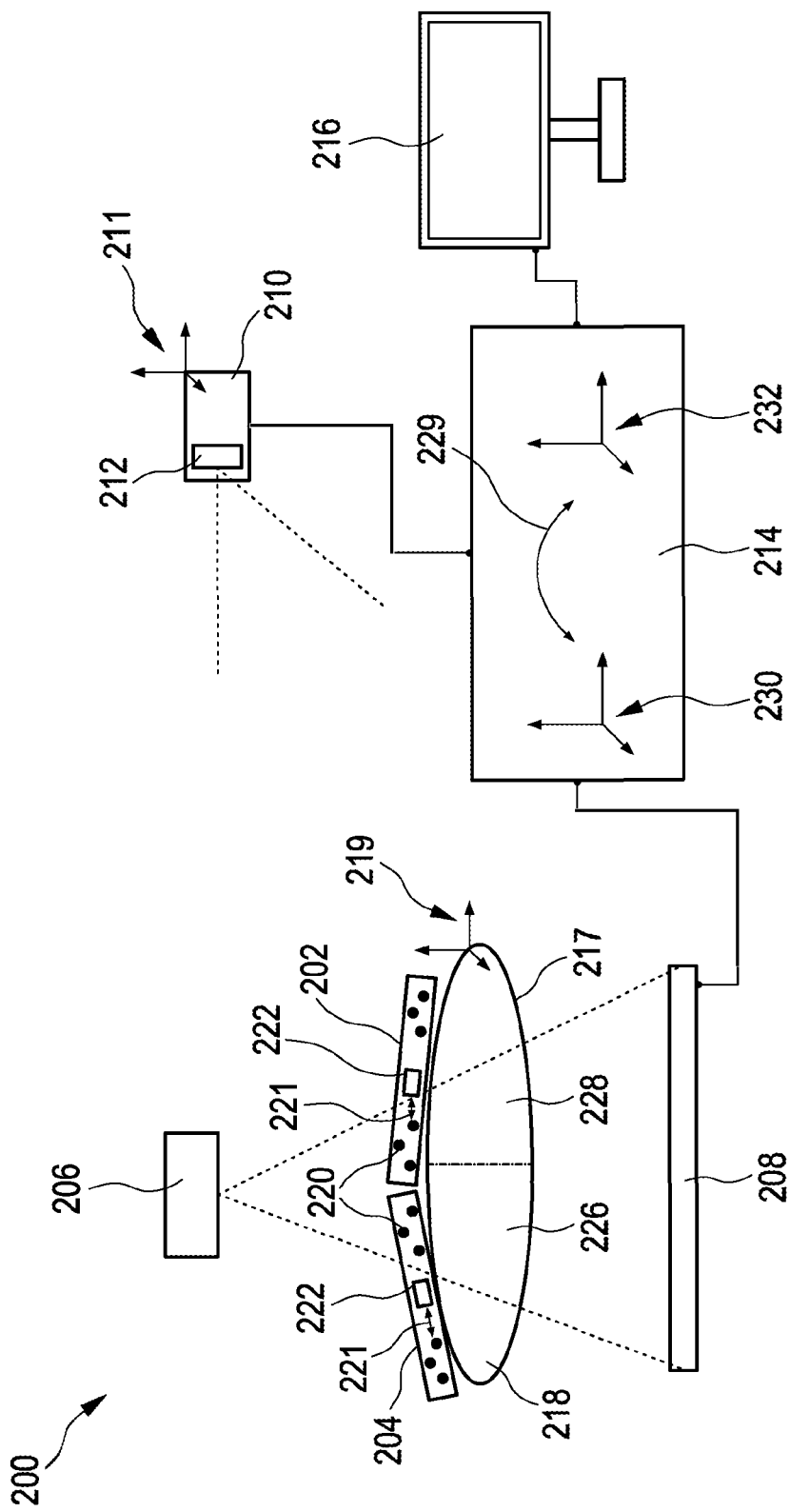
FIG. 2: shows navigation system that is configured for performing a registration method for automatically registering an object.

FIG. 2 shows a navigation system 200 that is configured for performing a registration method for automatically registering an object, e.g., for performing a registration method as described with reference to FIG. 1.

The navigation system 200 comprises two marker carriers 202, 204, an X-ray device comprising an X-ray source 206 and an X-ray detector 208, a position detection system 210 comprising a field generator 212 for generating an electromagnetic field, a registration unit 214 and a monitor 216.

By way of example, the marker carriers 202, 204 are arranged on the outer surface 217 of object 218. Each of the marker carriers 202, 204 has a plurality of fluoroscopically detectable markers 220 and a marker localization element 222 fixed on it. The marker carriers 202, 204 of the navigation system 200 can be configured the same way as a marker carrier described with reference to FIG. 1, e.g., a marker carrier can be a rigid or flexible marker carrier, or can be configured as described with reference to FIGS. 3 to 7. It is possible that the navigation system 200 comprises only one of the marker carriers 202, 204. For registering the object 218, the marker carrier can be displaced segment by segment. It is also possible that that the navigation system 200 comprises more than the two marker carriers 202, 204, wherein for registering object 218 the several marker carriers are arranged simultaneously, e.g., as a cluster or along a line, on the outer surface 217 of object 218. The navigation system can optionally comprise a reference localization element (not shown) that is configured for capturing an electromagnetic field and that is arranged stationary relative to the object 218. If present, the reference localization element can be fixed to the object 218 itself or can be fixedly arranged at a distance to the object 218. Position and orientation of marker carriers 202, 204 can be determined with the position detection system 210, e.g., relative to the position of a reference localization element.

The marker localization element 222 is configured for capturing an electromagnetic field that is generated by the field generator 212 of the position detection system 210 and for providing a sensor signal representing position and orientation of the marker localization element 222 in the electromagnetic field. If the marker localization element 222 comprises one or more sensor coils, a provided sensor signal represents a voltage that is induced in the coils and that depends on position and orientation of the marker localization element 222 in the electromagnetic field.

If one of the marker carriers 202, 204 is arranged on the outer surface 217 of the object 218, position and orientation of the marker localization element 222 can be determined and related to the position of a point on the outer surface 217 of object 218 in real space 219. Based on the known spatial relation between marker localization element 222 and the position of a point on the object's outer surface 217, the position of the point can be expressed in terms of coordinates of the position detection system's coordinate system 211 and vice versa.

The marker carrier 202 can be designed such that—if the marker carrier is arranged on the outer surface 217—the marker localization element 222 is arranged directly on the outer surface 217 such that the position of the marker localization element 222 determined with the position detection system 210 directly corresponds to the position of a point on the outer surface 217 of object 218. It is also possible that the marker carrier 202 is designed such that—if the marker carrier 202 is arranged on the outer surface 217—the marker localization element 222 is located at a distance above the outer surface 217 such that the coordinate in the position detection system's coordinate system 211 of a respective point on the outer surface 217 can be calculated by taking into account an offset that represents the relative distance between surface point and position of the marker localization element 222.

Since at least one of the fluoroscopically detectable markers 220 has an a priori known spatial relation (indicated by the arrow 221) to the marker localization element 222, the position of the marker can be expressed in terms of coordinates in the position detection system's coordinate system 211 and also in terms of coordinates in object space 219. By means of the position and orientation of the marker localization element 222 and, optionally, by using the at least one marker 220 with known relative distance and orientation to the marker localization element 222, a reference coordinate system 224 can be established at the object 218.

With the X-ray device, e.g., a C-arm, fluoroscopic image data can be recorded representing at least one of the marker carriers 202, 204 and at least one segment 226, 228 of the object 218. From recorded fluoroscopic image data, a fluoroscopic image can be generated by reconstructing image points from the fluoroscopic image data. Preferably, a fluoroscopic image is generated such that in the fluoroscopic image at least two markers 220 of each of the marker carriers 202, 204 are visible together with at least one segment 226, 228 of the object 218. This allows establishing a reference coordinate system at the preoperatively obtained model and finding a transformation function for transforming a coordinate of a model point of the model into coordinate of a point on the surface 217 of object 218 in real space.

Registration of the object, i.e., establishing a transformation function 229 for transforming coordinates between a reference coordinate system 230 at the object 218 and a reference coordinate system 232 at the model, is performed by the registration unit 214. Registration unit 214 is configured for accessing the generated fluoroscopic image and for relating image points of the generated fluoroscopic image to model points of a preoperatively obtained model of the object 218. Model data representing the preoperatively obtained model can be directly stored in the registration unit on a respective storage medium. Registration unit 214 is also connected to the position detection system 210 for accessing the determined position and orientation of the marker localization element 222.

The registration unit 214 of navigation system 200 is part of a data processing unit (not shown) of the navigation system 200. In an alternative embodiment a registration unit is part of position detection system. In yet another alternative embodiment position detection system and registration unit are components of the same data processing unit of a navigation system.

The registration unit 214 is configured to establish the reference coordinate system 230 at the object using the determined position and orientation of the marker localization element 222 and, optionally, the spatial relation between at least one marker 220 and the marker localization element 222. The registration unit 214 is configured to establish the reference coordinate system 232 at the model using the generated fluoroscopic image with at least two markers 220 being visible together with at least one segment. Establishing the reference coordinate system at the model can be achieved by the registration unit 214, since the registration unit 214 is configured for relating image points of the fluoroscopic image to respective model points of the model using the determined position and orientation of the marker localization element 222 and the known relative distance and orientation between the marker localization element 222 and at least one of the fluoroscopically detectable markers 220 and/or the spatial relation between another marker and the marker that has a known spatial relation to the marker localization element 222.

The known spatial relation between marker localization element 222 and markers 220 is provided as an input to the registration unit 214 as geometry data prior to registration. The geometry data can be provided as an input, e.g., by a user, or can be stored on a storage medium such that the registration unit 214 can read the geometry data from the storage medium. The geometry data can be provided in form of a constant vector or matrix representing the fixed spatial relation between, e.g., marker localization element 222 and one of the markers 220. In case the spatial relations between the marker localization element 222 and two or more markers 220 are known, a geometry data set can be provided as an input to the registration unit 214, the geometry data set comprising the geometry data of each of the known spatial relations.

In particular, the registration unit 214 is configured for segmentally relating image points of a generated fluoroscopic image to model points of the preoperatively obtained model.

The registration unit 214 is connected to the navigation system's monitor 216. For example, if an instrument (not shown) equipped with an instrument localization element is used with the navigation system 200, position and orientation of the instrument can be displayed on the monitor 216 in respective sectional images of the preoperatively obtained model. The navigation system 200 can be used for assisting a user in navigating an instrument relative to the object 218.

Figure 3:
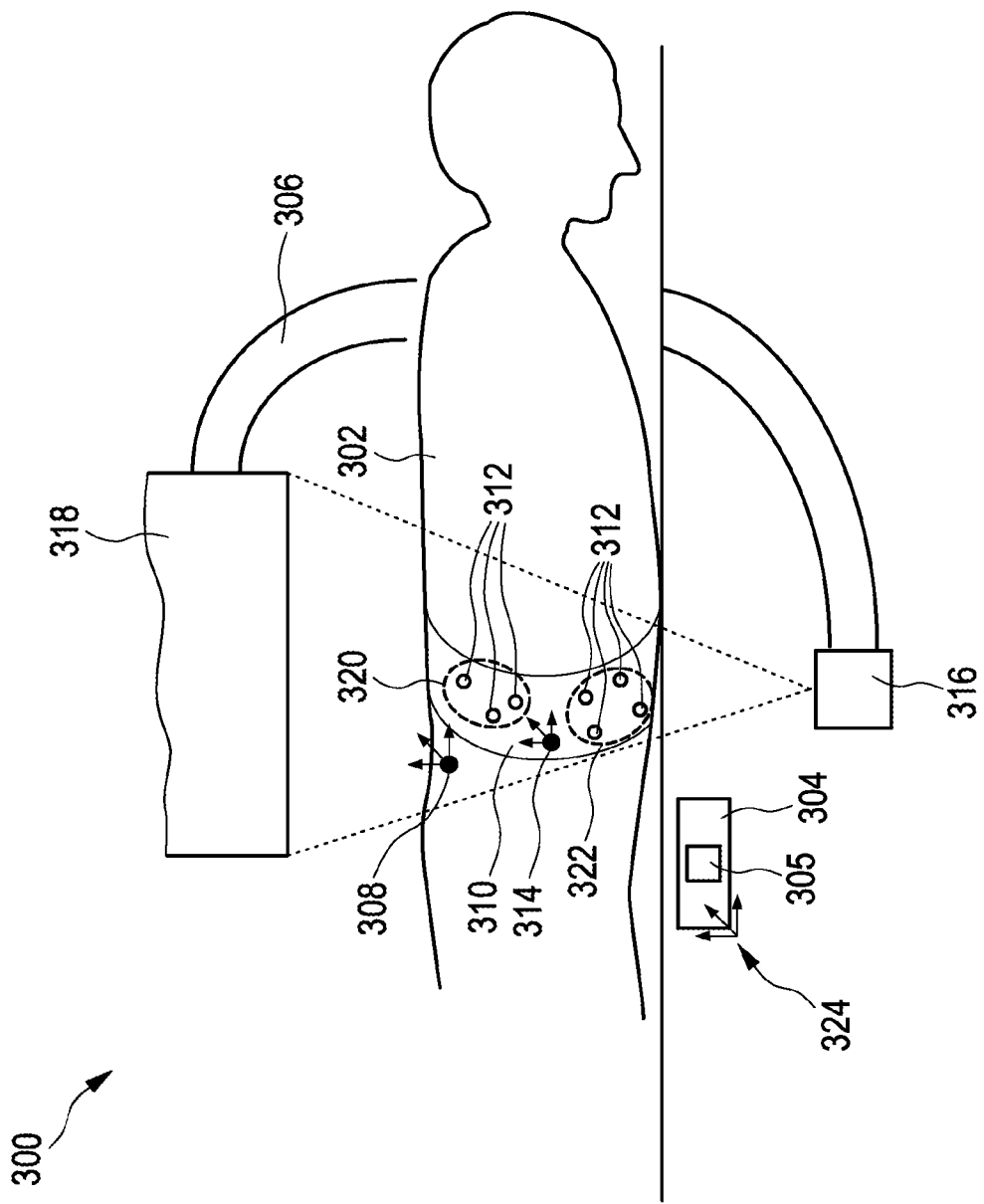
FIG. 3: shows a navigation system comprising a flexible marker carrier for registering a patient.

In FIG. 3, a navigation system 300 for registering a patient 302 is shown. The navigation system 300 comprises a position detection system 304, a registration unit 305, a C-arm 306, a reference localization element 308, and a marker carrier 310 having fluoroscopically detectable markers 312 and a marker localization element 314 fixed on it.

The marker carrier 310 is arranged on the skin of a patient 302. Marker carrier 310 is configured as a flexible belt such that when being arranged on the outer surface of an object, here, patient 302, the marker carrier 310 can adapt its shape to the topography of the outer surface.

The fluoroscopically detectable markers 312 fixed on the flexible belt 310 are arranged in groups of at least three markers that form a pattern that can be distinguished from patterns formed by other marker groups in a generated fluoroscopic image. In the instant example two patterns are shown. A first pattern 320 comprises three markers and a second pattern 322 comprises four markers. At a distance to the fluoroscopically detectable markers 312, marker localization element 314 is fixed on the flexible belt 310. For the flexible belt 310, the relative distance and orientation between all markers 312 and the marker localization element 314 are fixed. Here, relative distance and orientation between a respective one of the markers 312 and the marker localization element 314 are defined along the surface of the marker carrier 310. The relative distance refers to the shortest distance along the outer surface of the flexible marker carrier 310 between a respective marker 312 and the marker localization element 314.

The C-arm 306 has an X-ray source 316 and an X-ray detector 318 and is configured for generating a fluoroscopic image of the patient 302. In particular, a fluoroscopic image of the patient 302 can be generated such that at least two segments of the object are identifiable in the generated fluoroscopic image in that each of the segments is assigned to a different pattern 320, 322 formed by the markers 312. Since the markers 312 are arranged at fixed positions on the marker carrier 310 and form patterns that can be distinguished from other patterns, it is possible to determine the topography of the outer surface of the patient 302. Determining the topography of the outer surface of the patient 302 can be achieved because relative distance and orientation between the markers are known such that in the projection of the patterns visible in a generated fluoroscopic image a deviation of the pattern in terms of relative distance and orientation between the markers can be determined. From this deviation, an angle of a pattern with respect to the plane of projection visible in the fluoroscopic image can be determined and used for reconstructing the topography of the patient's skin.

The position detection system 304 is configured for determining position and orientation of the reference localization element 308 and for determining position and orientation of the marker localization element 314. In particular, position and orientation of the marker localization element 314 can be determined relative to position and orientation of the reference localization element 308. Preferably, the marker localization element 314 comprises two orthogonally arranged sensor coils and implements a six DOF sensor. In particular, in case the marker carrier 310 is arranged on the patient's skin, a determined position and orientation of the marker localization element 314 can be directly assigned to the position of a point on the skin of the patient 302. As a result of assigning position and orientation of the marker localization element to the position of a point on the skin of the patient 302, the respective point on the patient 302 can be expressed in terms of coordinates of the position detection system's coordinate system 324 and, vice versa, position and orientation of the marker localization element can be expressed in terms of coordinates in patient space. The marker localization element 314 can thus be used for establishing a reference coordinate system at the patient 302. For example, the reference coordinate system at the patient can be established by transforming the position detection system's coordinate system 324 such that its origin lies at the point on the patient's skin whose position and orientation coincide with the determined position and orientation of the marker localization element 314.

The position detection system 304 comprises the registration unit 305 which is configured for registering the patient 302. In particular, the registration unit 305 is configured for relating image points of a fluoroscopic image generated by the C-arm 306 to model points of a preoperatively obtained model of patient 302. The registration unit is configured for using the determined position and orientation of the marker localization element 314 and the known relative distance and orientation between each of the markers 312 and the marker localization element 314. Based on the determined position and orientation of the marker localization element and the known partial relation between the markers 312 and the marker localization element 314 it is possible to establish a reference coordinate system at the patient and at the preoperatively obtained model of the patient 302 and to find a transformation function for transforming coordinates between the two reference coordinate systems.

Figure 4:
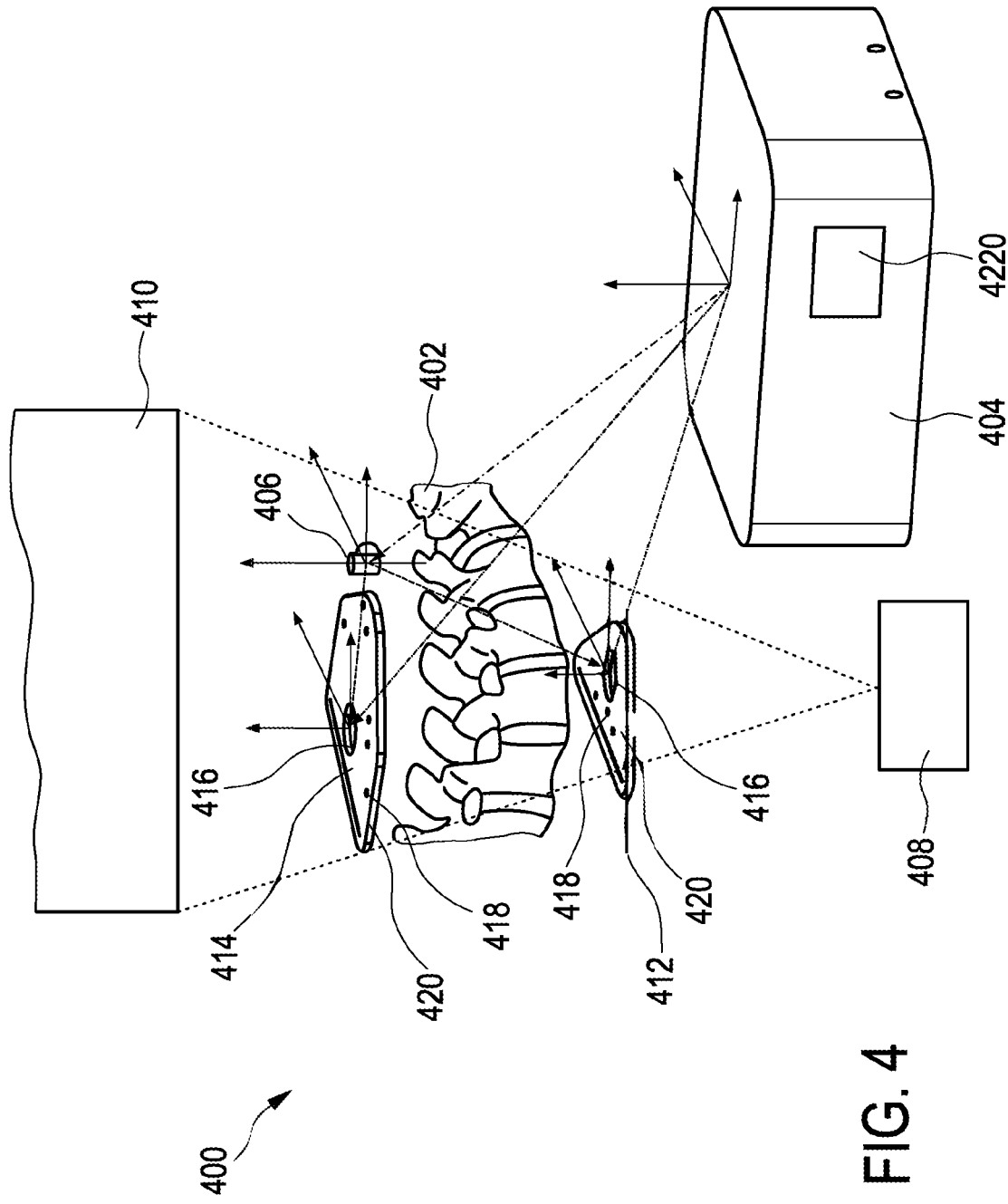
FIG. 4: shows a navigation system for performing automatic 2D registration of a patient's spine.

FIG. 4 shows a navigation system 400 for performing automatic 2D registration of a patient's spine 402 via interpolation.

The navigation system 400 comprises a position detection system 404, a reference localization element 406, an X-ray device having an X-ray source 408 and an X-ray detector 410, and two marker carriers 412, 414.

Each of the marker carriers 412, 414 is designed as a plate having a characteristic, approximately triangular base area and a circular perforation 416. Each of the marker carriers 412, 414 has a plurality of fluoroscopically detectable markers 418 and a marker localization element 420.

For registering the spine 402, on each of two opposing sides of the spine 402, a respective one of the two marker carriers 412, 414 is arranged. For example, one of the two marker carriers 412, 414 can be arranged at a distance to the spine at the back of a patient and the other marker carrier can be arranged on the opposite side of the patient, e.g., on the patient's stomach. If the spine 402 is exposed, marker carriers 412, 414 can also be arranged closer to the spine itself and can even be attached to the spine's vertebras. Since the spine 402 is arranged between the two marker carriers 412, 414, for automatic 2D registration of the spine 402, positions of points on the outer surface of spine can be determined by means of interpolation with respect to the two marker carriers 412, 414, and in particular, with respect to the determined position and orientation of a marker localization element 420 of each of the marker carriers 412, 414. Determining positions of points on the outer surface of spine by means of interpolation is possible since relative distance and orientation between the two marker carriers 412, 414 can be determined by detecting position and orientation of the marker localization element 420 of each of the marker carriers 412, 414 with the position detection system 404.

Position and orientation of the marker localization element 420 of each of the marker carriers 412, 414 can be determined with the position detection system 404, e.g., relative to the position and orientation of the reference localization element 406 in an electromagnetic field. The reference localization element 406 can be attached to the patient itself, for example, attached to the skin or, if the spine is exposed, can be directly attached to a spine's vertebra.

With the X-ray device, a fluoroscopic image can be generated of the two marker carriers 412, 414 arranged at opposite sides of the spine 404 such that in the fluoroscopic image at least two markers 418 of each of the two marker carriers 412, 414 and, preferably, two to four vertebras of the spine 402 are visible.

The position detection system 404 comprises a registration unit 422 that is configured for relating image points of a generated fluoroscopic image to model points of a preoperatively obtained model of the spine 402. Relating image points to model points can be performed by the registration unit 422 by using the determined position and orientation of a marker localization element 420 of each of the marker carriers 412, 414 and the known spatial relation between the fluoroscopically detectable markers 418 and the marker localization element 420 of a respective one of the two marker carriers 412, 414.

Figure 5:
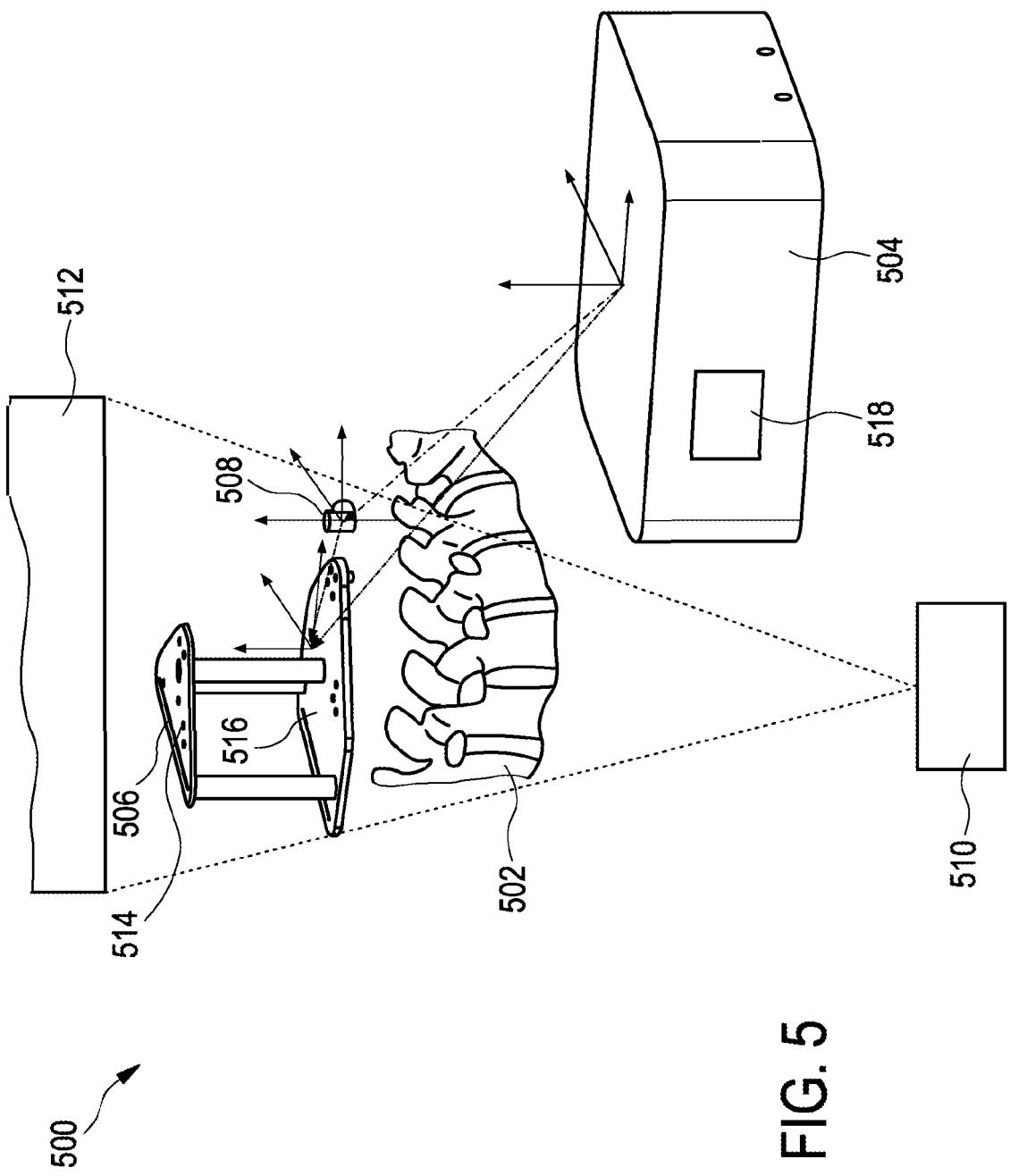
FIG. 5: shows a navigation system for performing automatic 2D registration of a patient's spine.

In FIG. 5, a navigation system 500 for performing automatic 2D registration of a patient's spine 502 via extrapolation is shown.

The navigation system 500 comprise a position detection system 504, a marker carrier 506, a reference localization element 508, and an X-ray device having an X-ray source 510 and an X-ray detector 512.

The marker carrier 506 comprises two plates that are arranged parallel to each other with respect to their basis surfaces. The two plates are rigidly connected to each other via three pins. By means of the pins, the two plates are arranged at a fixed relative distance to each other. On each of the two plates fluoroscopically detectable markers 514 are fixed and on one of the plates a marker localization element 516 is fixed. The relative distance and orientation between each of the markers 514 of the two plates and the marker localization element 516 are known.

For registering the spine 502, the marker carrier 506 is arranged on the spine 502. Arranging the marker carrier 506 on the spine 502 can comprise that the marker carrier 506 is arranged directly on the exposed spine 502 or is arranged at a distance to the spine 502 on the outer skin of a patient. The navigation system 510 can also comprise further marker carriers that are identical to marker carrier 506 and that can be arranged simultaneously on the patient, for example, along the length of the patient's spine.

If the marker carrier 506 is arranged on the spine, position and orientation of the marker localization element 516 can be determined with the position detection system 504, for example, relative to the position of the reference localization element 508. If the spine 502 is exposed, the reference localization element 508 can be rigidly attached directly to a spine's vertebra. However, the reference localization element 508 can also be attached to the outer skin of a patient or can be arranged rigidly at a distance next to a patient. From the determined position and orientation of the marker localization element 516 and the position and orientation of the reference element 508 the position of a point on the spine 502 in the position detection system's coordinate system can be extrapolated.

Of the marker carrier 506, a fluoroscopic image can be generated with the X-ray device such that in the fluoroscopic image at least two markers 514 are visible together with at least one segment, e.g., at least one vertebra, of the spine 502.

The position detection system 504 comprises a registration unit 518 that is configured for accessing the generated fluoroscopic image and the determined position and orientation of the marker localization element 516 in order to relate image points of the generated fluoroscopic image to model points of a preoperatively obtained model of the spine 502. For relating image points to model points the registration unit 518 uses the determined position and orientation of the marker localization element 516 and the known spatial relation between the markers 514 and the marker localization element 516.

Figure 6:
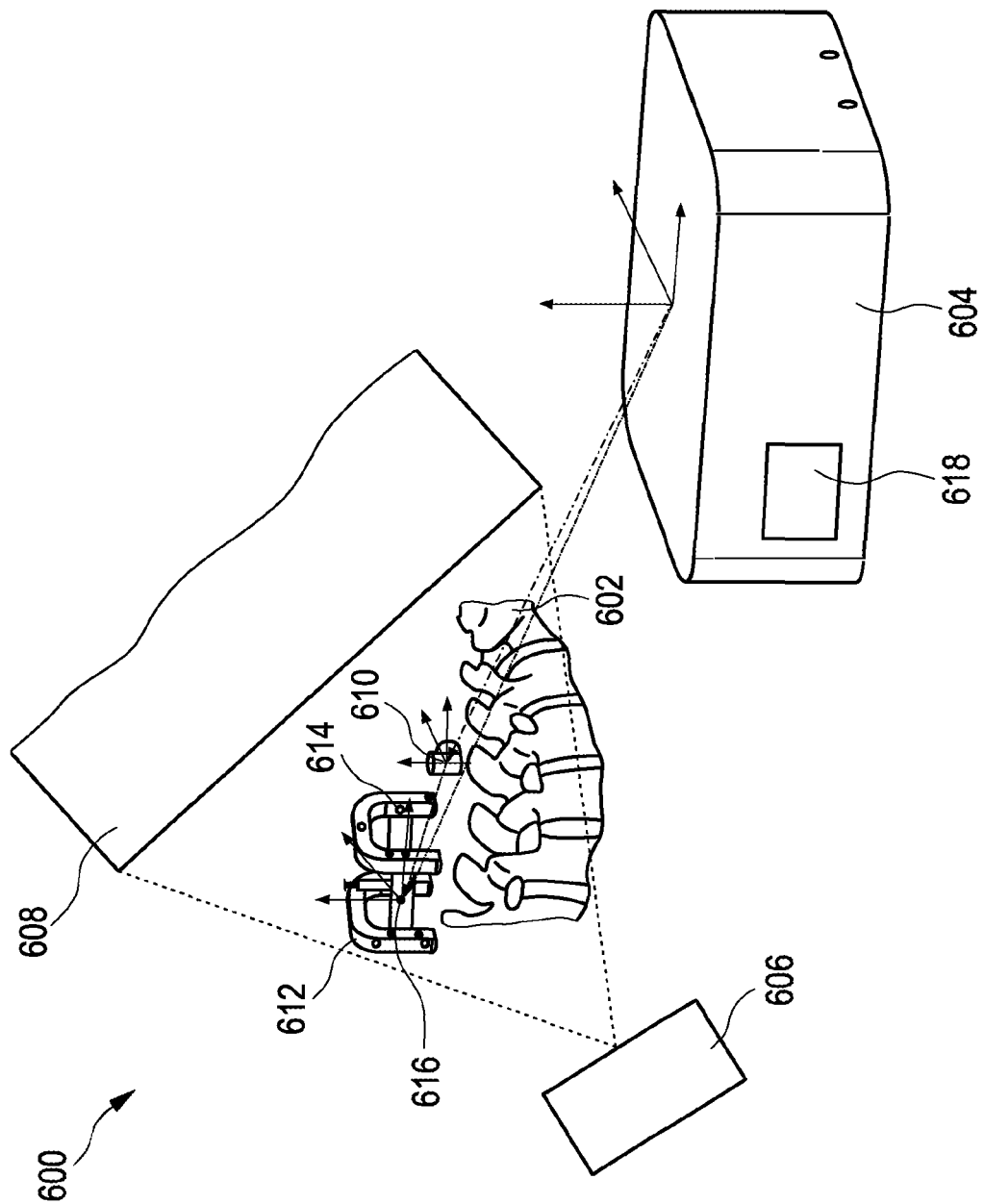
FIG. 6: shows a navigation system for performing automatic 3D registration of a patient's exposed spine.

In FIG. 6, a navigation system 600 is shown that can be used, e.g., for registering an exposed spine 602.

The navigation system 600 comprises a position detection system 604, an X-ray device having an X-ray source 606 and an X-ray detector 608, a reference localization element 620 and a marker carrier 612.

The marker carrier 612 has a plurality of fluoroscopically detectable markers 614 and a marker localization element 616 fixed on it. The marker carrier 612 is implemented in the shape of a cage such that marker carrier 612 can be arranged on the spine 602 to enclose an exposed vertebra. Thereby, automatic 3D registration of the spine is possible. Marker carrier 612 this characterized in that the fluoroscopically detectable markers 614 have a known spatial relation to each other and to the marker localization element 616.

Position and orientation of the marker localization element can be determined with the position detection system 604. In particular, position and orientation of the marker localization element 616 can be determined by the position detection system 604 relative to the position and orientation of the reference localization element 610 which is rigidly fixed to a spine's vertebra.

It is possible that the navigation system 600 comprises further marker carriers which can be configured the same way as marker carrier 612. If the navigation system 600 comprises cage-shaped marker carriers, the several marker carriers can be arranged along the exposed spine 602 enclosing the exposed vertebras.

With the X-ray device, a fluoroscopic image of the marker carrier 612 can be generated together with at least one segment of the spine. A segment can comprise one vertebra, e.g., the vertebra on which the marker carrier 612 is arranged such that in a generated fluoroscopic image, preferably, this vertebra is visible together with two to three neighbouring vertebras.

The position detection system 604 of the navigation system 600 comprises a registration unit 618 that is configured for relating image points of a generated fluoroscopic image to model points of a preoperatively obtained model of the spine. For relating image points to model points, the registration unit 618 is configured to use the determined position and orientation of the marker localization element 616 and the known relative distance and orientation between at least one of the markers 614 and the marker localization element 616.

Figure 7:
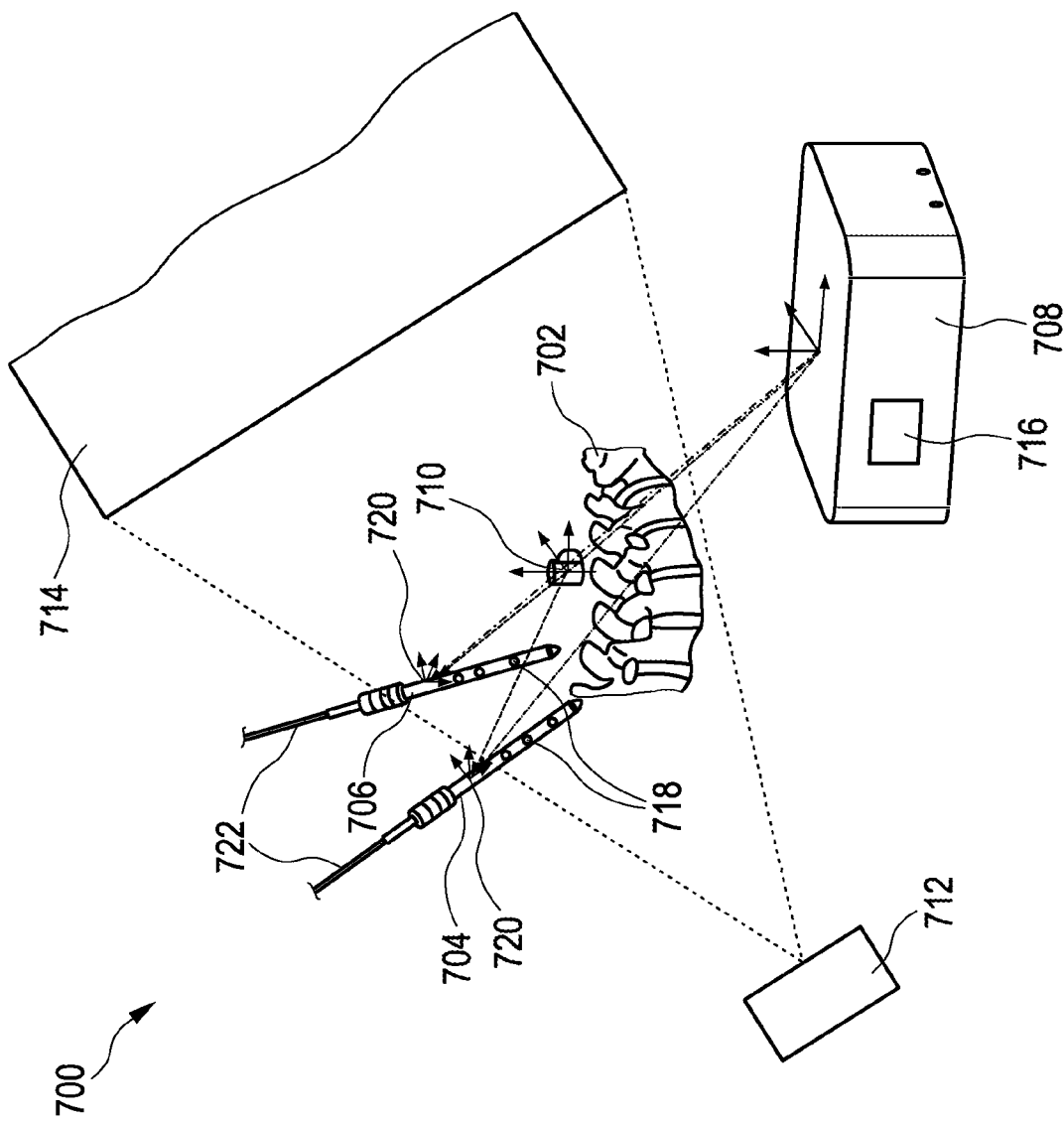
FIG. 7: shows a navigation system for performing minimal invasive automatic 3D registration of a patient's spine.

In FIG. 7, a navigation system 700 is shown that can be used for performing automatic 3D registration of a spine 702 in a minimal invasive procedure.

The navigation system 700 comprises two marker carriers 704, 706, a position detection system 708, a reference localization element 710, and an X-ray device having an X-ray source 712 and an X-ray detector 714.

Each of the two marker carriers 704, 706 is implemented in the shape of a stick and comprises a plurality of fluoroscopically detectable markers 718 arranged along the length of the stick. The marker carriers 704, 706, each, have a marker localization element 720 fixed on it, wherein relative distance and orientation between the markers 718 and the marker localization element 720 are known. Each marker localization element 720 of the marker carriers 704, 706 is connected via a cable 722 to the position detection system 708 for transmitting sensor signals representing position and orientation of the respective marker localization element 720 in an electromagnetic field that is generated by a position detection system's field generator (not shown). In particular, position and orientation of the marker localization element 720 can be determined by the position detection system 708 relative to the position and orientation of the reference localization element 710 that is rigidly fixed to a spine's vertebra.

In a minimal invasive procedure, the two marker carriers 704, 706 can be inserted into a patient's body and navigated to a patient's spine 702 such that on each of two opposite sides of the spine a respective one of the marker carriers 704, 706 is arranged. Thereby, it is possible to perform automatic 3D registration of the spine 702.

With the two marker carriers 704, 706 being arranged next to the patient's spine 702, a fluoroscopic image can be generated by means of the X-ray device. Preferably, the fluoroscopic image is generated such that in the fluoroscopic image at least two markers 718 of each of the marker carriers 704, 706 are visible together with at least one segment of the spine 702. For example, it is preferred that three to four vertebras are visible in a generated fluoroscopic image.

The navigation system's position detection system 708 comprises a registration unit 716 that is configured for relating image points of a generated fluoroscopic image to model points of a preoperatively obtained model of the patient's spine 702. For relating image points to model points, the registration unit 716 is configured to use a determined position and orientation of the marker localization element 720 of each of the marker carriers 704, 706 and the known spatial relation between at least one of the markers 718 and the respective marker localization element 720.

The invention claimed is:

1. A method for automatically registering an object, the method comprising the steps of
providing a preoperatively obtained model of the object,
providing at least one marker carrier having a plurality of fluoroscopically detectable markers and at least one marker localization element comprising at least one sensor coil fixed on said marker carrier, wherein
the at least one marker localization element being configured to provide a sensor signal representing position and orientation of the marker localization element in an electromagnetic field, and
relative distance and orientation between at least one marker localization element and at least one marker of the plurality of markers are known,
arranging at least one marker carrier on an outer surface of the object, generating at least one fluoroscopic image of at least one marker carrier arranged on the outer surface together with at least one segment of the object in such a way that at least two markers of at least one marker carrier are visible in the generated fluoroscopic image together with at least one segment of the object, determining position and orientation at least of one marker localization element of the arranged marker carrier in an electromagnetic field, and relating image points of the generated fluoroscopic image to model points of said preoperatively obtained model using the determined position and orientation of at least one marker localization element and the known relative distance and orientation between at least one marker localization element and at least one marker of the plurality of markers and/or a known spatial relation between a further marker of the plurality of markers and the at least one marker that has a known relative distance and orientation to at least one marker localization element, characterized by the step of detecting a relative movement of an element of the object by determining a deviation of at least one model point of the preoperatively obtained model from a corresponding image point of the generated fluoroscopic image.

2. The method of claim 1, wherein said model points are points of a model surface of the preoperatively obtained model and wherein said model surface corresponds to the outer surface of the object.

3. The method of claim 1, wherein a flexible marker carrier is arranged on the object's outer surface, the plurality of markers is fixed in such a way on said marker carrier that respective groups of three markers each form a pattern that can be distinguished from patterns formed by other marker groups in the generated fluoroscopic image, and at least two segments of the object are identifiable in the at least one generated fluoroscopic image in that each of the segments is assigned to a different pattern formed by said markers.

4. The method of claim 1, wherein at least two marker carriers are simultaneously arranged on the object's outer surface, the at least one fluoroscopic image is generated of at least two segments of the object in such a way that for each segment at least two markers of an arranged marker carrier are visible in the generated fluoroscopic image together with the respective segment, and a spatial relation between the segments of which the fluoroscopic image was generated is determined using positions of those markers that are visible in the generated fluoroscopic image.

5. The method of claim 1, wherein in successive steps the marker carrier is arranged on the object's outer surface, in each of the successive steps a fluoroscopic image of the arranged marker carrier together with at least one segment is generated in such a way that at least two markers of the marker carrier are visible in the fluoroscopic image together with a respective segment of the object, and a spatial relation between the segments of which the fluoroscopic images were generated is determined using positions of those markers that are visible in the respective fluoroscopic images.

6. The method of claim 1, wherein for each generated fluoroscopic image of one or more segments, image points of a respective one of these fluoroscopic images are segmentally related to model points of said preoperatively obtained model.

7. The method of claim 6, wherein from image points of at least two segments related to respective model points and a known spatial relation between the at least two segments a registration error is determined.

8. The method of claim 1, further comprising the step of visualizing the preoperatively obtained model on an image display unit in such a way that depending on the relating of image points to model points the visualized model is aligned such that the viewing direction on said model on the image display unit corresponds to the recording direction from which fluoroscopic image data used for generating the fluoroscopic image of at least one segment were recorded.

9. The method of claim 1, further comprising the step of segmentally adapting the preoperatively obtained model of the object using said determined deviation.

10. The method of claim 1, further comprising the steps of providing an instrument having an instrument localization element comprising at least one sensor coil for determining position and orientation relative to an electromagnetic field, determining position and orientation of the instrument localization element in an electromagnetic field relative to the position and orientation of at least one marker localization element, visualizing the adapted model of the object on an image display unit together with at least a part of said instrument, wherein position and orientation of said instrument in the visualization of said model are adapted using the determined deviation of at least one model point from a corresponding image point of the generated fluoroscopic image.

11. The method of claim 10, wherein adapting position and orientation of said instrument in the visualization of said adapted model is performed segmentally for each segment of the object that is visible in the generated fluoroscopic image.

12. The method of claim 1, further comprising the steps of arranging at least one reference localization element comprising at least one sensor coil in a fixed spatial relation to the object, the at least one reference localization element being configured to provide a reference sensor signal representing position and orientation of the reference localization element in an electromagnetic field, and determining position and orientation of at least one marker localization element in an electromagnetic field relative to position and orientation of at least one reference marker localization.

13. The method of claim 12, comprising the steps of determining position and orientation of at least one marker localization element relative to at least one reference localization element at a first instant of time and at a later further instant of time, and detecting a change in position and/or orientation of said marker localization element relative to position and orientation of at least one reference localization element at the later instant of time in relationship to the earlier first instant of time.

14. The method of claim 1, wherein
the object is a patient's spine and the at least one segment of the spine comprises one or more vertebras,
the preoperatively obtained model is a model of at least a part of the spine,
the at least one marker carrier is arranged on the spine,
at least one fluoroscopic image is generated of at least the segment comprising the vertebra that has the marker carrier arranged on the segment in such a way that at least two of the plurality of fluoroscopically detectable markers of the marker carrier are visible together with at least one vertebra, and
for each generated fluoroscopic image of one or more vertebras, image points of a respective one of these fluoroscopic images are segmentally related to model points of said preoperatively obtained spine model.

15. The method of claim 14, wherein image points of the fluoroscopic image that are associated with a visible vertebra are related to respective model points of the same vertebra in the preoperatively obtained spine model.

16. The method of claim 14, wherein several marker carriers are arranged simultaneously along the spine during spine surgery and wherein
at least one fluoroscopic image is generated at least of the vertebras that have the marker carriers arranged on the vertebras, and
for each generated fluoroscopic image, image points of the fluoroscopic image that are associated with a visible vertebra are related to respective model points representing the same vertebra in the preoperatively obtained spine model.

17. The method of claim 14, wherein a relative movement of at least one of the spine's vertebras is detected intraoperatively by determining a deviation of at least one model point of the preoperatively obtained spine model from a corresponding image point of the generated fluoroscopic image.

18. The method of claim 14, wherein with at least one marker carrier being arranged on a vertebra for intraoperatively registering the spine or with at least one marker carrier being arranged on the spine only for intraoperatively registering the spine and removed afterwards, spinal fusion is performed.

19. The method of claim 18, wherein spinal fusion includes that two or more vertebras are joint by means of a pedicel screw, a plate or a cage.

20. The method of claim 14, wherein with at least one marker carrier being arranged on a vertebra for intraoperatively registering the spine or with at least one marker carrier being arranged on the spine only for intraoperatively registering the spine and removed afterwards, a polyaxial screw is screwed into the respective vertebra having the at least one marker carrier arranged on the vertebra.

21. The method of claim 14, wherein with at least one marker carrier being arranged on a vertebra for intraoperatively registering the spine or with at least one marker carrier being arranged on the spine only for intraoperatively registering the spine and removed afterwards, minimally invasive spine surgery is performed.

22. The method of claim 14, wherein with at least one marker carrier being arranged on a vertebra for intraoperatively registering the spine or with at least one marker carrier being arranged on the spine only for intraoperatively registering the spine and removed afterwards, bone marrow biopsy is performed on the spine.

23. The method of claim 14, comprising that a Jamshidi needle is inserted into the spine.

24. The method of claim 14, wherein with at least one marker carrier being arranged on a vertebra for intraoperatively registering the spine or with at least one marker carrier being arranged on the spine only for intraoperatively registering the spine and removed afterwards, fine-needle aspiration biopsy (FNAB) is performed by inserting a hollow needle into a patient's body.

25. The method of claim 14, wherein the at least one marker carrier being arranged on a vertebra for intraoperatively registering the spine or the at least one marker carrier being arranged on the spine only for intraoperatively registering the spine and removed afterwards, and wherein a cannulated medical instrument is inserted into a patient's body comprising at least one instrument localization element for providing position and orientation information.

26. The method of claim 14, wherein the at least one marker carrier being arranged on a vertebra for intraoperatively registering the spine or the at least one marker carrier being arranged on the spine only for intraoperatively registering the spine and removed afterwards, and wherein a cannulated medical instrument is inserted into a patient's body for providing a working channel for an additional medical instrument, where the additional medical instrument comprises at least one instrument localization element for providing position and orientation information.

27. A marker carrier for use in a registration method, wherein
the marker carrier is flexible and has a plurality of fluoroscopically detectable markers and at least one marker localization element comprising at least one sensor coil fixed on the marker carrier,
the at least one marker localization element being configured to provide a sensor signal representing position and orientation of the marker localization element in an electromagnetic field, and
relative distance and orientation between at least one marker localization element and at least one marker of the plurality of markers are known, and
wherein the registration method comprises
providing a preoperatively obtained model of the object,
providing at least one marker carrier having a plurality of fluoroscopically detectable markers and at least one marker localization element comprising at least one sensor coil fixed on the marker carrier, wherein the at least one marker localization element being configured to provide a sensor signal representing position and orientation of the marker localization element in an electromagnetic field, and relative distance and orientation between at least one marker localization element and at least one marker of the plurality of markers are known,
arranging at least one marker carrier on an outer surface of the object,
generating at least one fluoroscopic image of at least one marker carrier arranged on the outer surface together with at least one segment of the object in such a way that at least two markers of at least one marker carrier are visible in the generated fluoroscopic image together with at least one segment of the object,
determining position and orientation at least of one marker localization element of the arranged marker carrier in an electromagnetic field, and
relating image points of the generated fluoroscopic image to model points of said preoperatively obtained model using the determined position and orientation of at least one marker localization element and the known relative distance and orientation between at least one marker localization element and at least one marker of the plurality of markers and/or a known spatial relation between a further marker of the plurality of markers and the at least one marker that has a known relative distance and orientation to at least one marker localization element, characterized by the step of detecting a relative movement of an element of the object by determining a deviation of at least one model point of the preoperatively obtained model from a corresponding image point of the generated fluoroscopic image.

\* \* \* \* \*